(12) United States Patent
Uber, III et al.

(10) Patent No.: US 8,470,298 B2
(45) Date of Patent: Jun. 25, 2013

(54) METHOD OF PREPARING A MEDIUM WITH BUBBLES FORMED THEREIN FOR CONTEMPORANEOUS INJECTION

(75) Inventors: Arthur E Uber, III, Pittsburgh, PA (US); David M Griffiths, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 1096 days.

(21) Appl. No.: 10/798,876

(22) Filed: Mar. 11, 2004

(65) Prior Publication Data

US 2004/0253183 A1 Dec. 16, 2004

Related U.S. Application Data

(63) Continuation of application No. PCT/US03/18445, filed on Jun. 10, 2003, and a continuation of application No. 10/352,392, filed on Jan. 27, 2003, now abandoned.

(60) Provisional application No. 60/351,923, filed on Jan. 25, 2002.

(51) Int. Cl.
*A61B 8/00* (2006.01)
*A61K 49/00* (2006.01)

(52) U.S. Cl.
USPC .............................. 424/9.1; 424/9.5; 424/9.52

(58) Field of Classification Search
USPC ....................................................... 424/9.52
See application file for complete search history.

(56) References Cited

U.S. PATENT DOCUMENTS

| | | | |
|---|---|---|---|
| 5,088,499 A | 2/1992 | Unger | |
| 5,228,446 A | 7/1993 | Unger et al. | |
| 5,240,598 A | 8/1993 | Portier et al. | |
| 5,315,997 A | 5/1994 | Widder et al. | |
| 5,569,181 A | 10/1996 | Heilman | |
| 5,580,575 A | 12/1996 | Unger et al. | |
| 5,605,673 A | 2/1997 | Schutt et al. | |
| 5,739,508 A | 4/1998 | Uber, III | |
| 5,806,519 A | 9/1998 | Evans, III | |
| 5,840,026 A | 11/1998 | Uber, III | |
| 5,843,037 A | 12/1998 | Uber, III | |
| 5,885,216 A * | 3/1999 | Evans et al. | 600/431 |
| 6,149,627 A | 11/2000 | Uber, III | |
| 6,183,725 B1 | 2/2001 | Yan et al. | |
| 6,231,513 B1 * | 5/2001 | Daum et al. | 600/458 |
| 6,302,845 B2 | 10/2001 | Shi et al. | |
| 6,306,117 B1 | 10/2001 | Uber, III | |
| 6,317,623 B1 | 11/2001 | Griffiths | |
| 6,397,098 B1 * | 5/2002 | Uber et al. | 600/431 |
| 6,468,506 B1 * | 10/2002 | Rossling et al. | 424/9.5 |

FOREIGN PATENT DOCUMENTS

| | | |
|---|---|---|
| EP | 135822 A2 * | 4/1985 |
| WO | WO 9640282 A2 * | 12/1996 |
| WO | WO 99/27981 | 6/1999 |
| WO | WO 00/53242 | 3/2000 |

OTHER PUBLICATIONS

Brain, Marshall, "How Does a Bubble Jet Printer Work?", How Stuff Works Web Page (Mar. 10, 2004).
Inkjet Printer Head Technology, Colour Printer Head Technology, Industrial Technology Web Page (Jun. 1996).
International Counterpart Application No. PCT/US03/18445 International Search Report.

* cited by examiner

*Primary Examiner* — Michael G Hartley
*Assistant Examiner* — Melissa Perreira
(74) *Attorney, Agent, or Firm* — James R. Stevenson

(57) ABSTRACT

An apparatus, system or method enables microbubbles to be created on demand for use as the contrast agent within a contrast medium administrable to a patient for purposes of a medical procedure. The system comprises a reservoir, a pressurizing device, a microbubble generator, and a controller. The reservoir stores a liquid. The pressurizing device conveys the liquid, along with the medium formed therewith, through the system. The microbubble generator is used to create the microbubbles within the liquid to form the medium. The microbubble generator has an inlet for receiving the liquid and an outlet for communication of the medium to the patient. The controller controls the operation of the system so that the microbubbles created by the microbubble generator are generated according to the demands of the medical procedure and are administrable within the medium to the patient.

53 Claims, 12 Drawing Sheets

BOTTOM

TOP

SECTION A-A

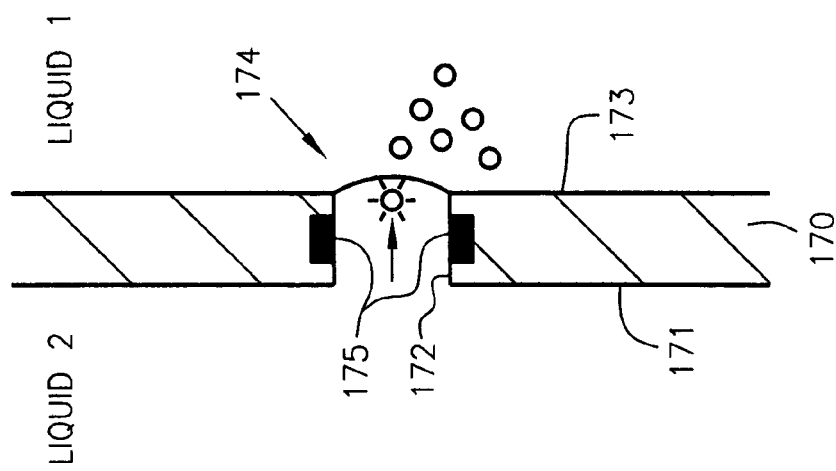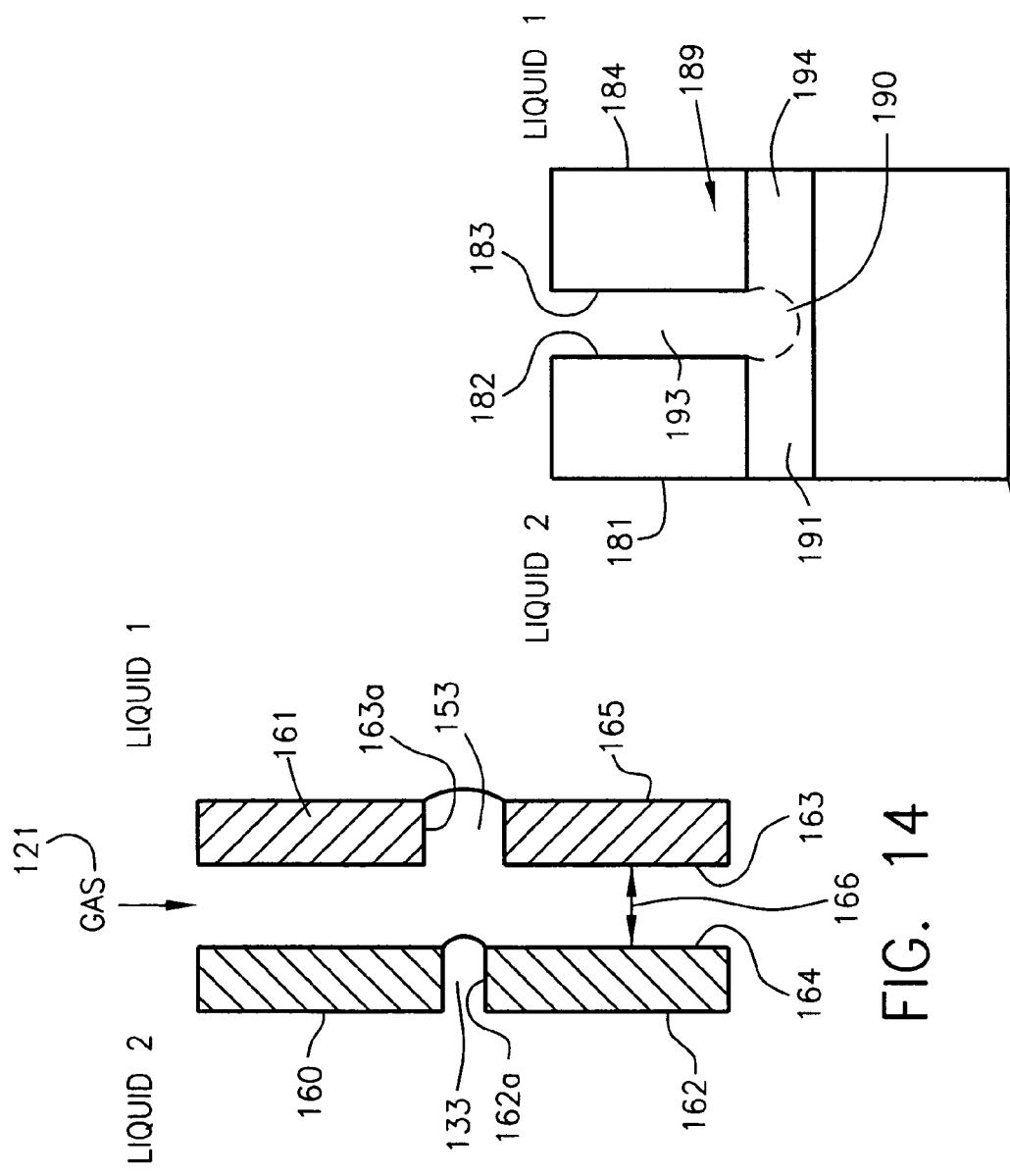

METHOD OF PREPARING A MEDIUM WITH BUBBLES FORMED THEREIN FOR CONTEMPORANEOUS INJECTION

CROSS-REFERENCE TO RELATED APPLICATION(S)

This application claims the benefit of U.S. Provisional Application 60/351,923 titled Apparatus, System And Method For Generating Bubbles On Demand, filed Jan. 25, 2002; U.S. application Ser. No. 10/352,392 titled Apparatus, System And Method For Generating Bubbles On Demand, filed Jan. 27, 2003; and PCT/US03/18445 titled Apparatus, System And Method For Generating Bubbles On Demand, filed Jun. 10, 2003. These provisional, non-provisional and international applications have been assigned to the assignee of the invention disclosed below, and their teachings are incorporated into this document by reference.

FIELD OF THE INVENTION

The invention generally relates to bubble contrast media of the type used for diagnostic imaging and therapeutic procedures. More particularly, the invention relates to apparatuses, systems and methods for preparing on demand, for injection into a patient, bubble contrast media for obtaining high contrast images of the anatomy of the patient during a diagnostic imaging procedure and/or for the delivery of therapy to the patient.

BACKGROUND OF THE INVENTION

The following background information is provided to assist the reader to understand the invention disclosed below and the environment in which it will typically be used. The terms used herein are not intended to be limited to any particular narrow interpretation unless clearly stated otherwise in this document.

Ultrasound is a well-known technique that uses sound waves to produce on a display screen images of the region of the body being scanned. It does this by emitting ultrasonic waves—at frequencies in the range of 1 to 20 Megahertz (MHz)—into the body and then producing an image from the waves that are reflected by the tissues in the area being scanned. Although other techniques (e.g., computerized tomography (CT), positron emission tomography (PET), magnetic resonance imaging (MRI) and magnetic resonance angiography (MRA)) can be used to produce images of the body, they do so using extremely expensive equipment. In addition, although CT and PET scanning techniques are considered reasonably safe, they obtain images using ionizing radiation, which can pose a risk to human health particularly upon repeated exposure. The sound waves used during an ultrasound procedure, however, are comparatively risk free.

An ultrasound system typically features a display screen, a control unit, and a transducer, which is often referred to as a probe. The transducer transmits and receives ultrasonic energy along a beam. When ultrasonic waves traveling through one tissue hit a boundary with a second tissue, some of them pass into the second tissue, and some are reflected back to the transducer. The exact fraction of the energy that is absorbed or reflected depends on how different the two tissues are from each other. This is known as the acoustic impedance of the tissue, and is related to the density and composition of the tissue and the speed of sound through it. The greater the difference in impedance between two tissues, the more sound energy will be reflected back at their interface. Interfaces between solid tissues, the skeletal system, and various organs, and even tumors, are readily imaged by ultrasound techniques. Ultrasound thus yields especially sharp images where there are distinct variations in the density or compressibility of the tissue, such as at the tissue interfaces. If the acoustic impedance difference is too great, however, a good image may not be created because too much energy is reflected.

A transducer is typically equipped with both a transmitter and a receiver of ultrasonic waves. Because air and skin have different ultrasonic impedances, a coupling medium (i.e., a layer of gel) is applied to the region of interest to match the impedance of the piezoelectric crystals in the transducer more closely to the impedance of the skin of the patient, thus allowing the ultrasonic waves to enter the body more readily. In operation, the transducer is periodically driven by an electrical pulse, which causes its transmitter to periodically emit a pulse of ultrasonic energy. During a scanning procedure, as the transducer is moved over the region of interest, only those waves that reflect or scatter at the tissue interfaces are picked up by the receiver. Because the transducer transmits and receives ultrasonic waves primarily along a beam, when an echo is received, the interface causing the echo must therefore be within the path of the beam. In addition, the time that the reflected energy or "echo" takes to arrive at the receiver from a given interface depends on the distance between the interface and the surface of the skin, which provides an indication of the depth of the interface. Depending on how it is configured, the control unit of an ultrasound system may be programmed to process the information obtained during a scan in different ways to provide different images (e.g., A-Scans (Amplitude Scans), B-Scans (Brightness), Real-Time B-Scans, and Doppler) of the observed region on the display screen. Differences in the reflected energy are typically made to appear on the display screen as different colors or different shades of gray.

Ultrasound provides images of sufficiently high quality for many diagnostic applications. In certain types of applications, however, a contrast fluid or "medium" will be administered to the patient to enhance the quality of the images that can be obtained during a scanning procedure. A contrast medium contains what is referred to as a contrast agent, which can take the form of suspended or dispersed entities such as microbubbles, microspheres or solid particles. Soon after injection into a patient, the contrast medium reaches the region of interest. In response to the incident ultrasonic waves, the contrast medium yields a pronounced difference in the reflected energy between the contrast agent contained therein and the surrounding tissues. In this way, the contrast agent serves to increase or enhance the image contrast between the tissues in the region of interest, and thereby enhance the resolution of the images obtained during the scanning procedure. Besides being used for imaging, contrast media can also be injected into various body cavities or tissues as necessary for diagnostic or therapeutic procedures.

Contrast media are particularly well suited for studying the adequacy of blood flow in the organs and other tissues. For example, when a contrast medium is injected into the blood stream, the reflected ultrasound energy will be Doppler shifted due to the flow of blood in which the contrast agents are being carried. This Doppler shift allows the speed, and thus the adequacy, of the blood flow to be ascertained quite readily. Contrast agents can also be excited so that they radiate ultrasonic energy at a harmonic of the incident ultrasonic energy. Harmonic imaging with the use of a contrast medium can be used to increase the effectiveness of the contrast agent.

The most commonly used contrast media typically employ microbubbles (i.e., small bubbles typically 3-10 microns (μm) in diameter) as the contrast agent. Typically containing a gas such as air, a perfluorocarbon, or carbon dioxide, microbubbles are formed with the use of foaming agents, surfactants or encapsulating chemicals. Once injected intravenously, the microbubbles provide a substance in the blood that is of a different density and a much higher compressibility than the flowing blood and adjacent tissues. Microbubbles thus constitute an excellent means for reflecting and scattering ultrasound energy, which makes them easily imaged with ultrasound techniques. The contrast media can also be excited in such a way that the microbubbles are destroyed, and the energy released during the popping of the microbubbles is used to create the image.

Contrast media suitable for use in ultrasound are supplied in a number of forms. U.S. Pat. No. 5,605,673 to Schutt et al. and U.S. Pat. No. 6,317,623 B1 to Griffiths et al., incorporated herein by reference, discuss many of these in detail. Some contrast media take the form of powders to which a liquid is added just before use. The particles in the powder cause gas microbubbles to coalesce around them. The powder must be mixed with a liquid, and the mixture agitated with a precise degree of vigor, to obtain microbubbles having optimum characteristics. Another type of contrast medium supplied in liquid form requires hypobaric or pressure activation. A third type of contrast medium is a liquid that must be agitated vigorously. There are no solid particles to act as nucleation sites, but the liquid is a mixture of several components that make relatively stable small bubbles. A fourth type of contrast medium uses "hard" spheres filled with a gas. These contrast media are typically supplied as a powder that is mixed with a liquid. The goal is to suspend the spheres in the liquid without breaking them. Though such spheres have a shell that is hard compared to a liquid, they are very small and relatively fragile. It is possible for the solid particles themselves to act to scatter ultrasonic energy, but the acoustical properties of the solid spheres are not as different from water as those of a gas. Solid particles are therefore not as efficient or effective as scatterers of ultrasonic energy. Solid particles, however, have the advantage that they are much more robust and longer lasting.

FIG. 1 illustrates an example of the current practice in ultrasound imaging. The contrast medium often comes within a single-use vial 10 in which a fluid and an appropriate gas have been sealed. After mixing or preparation as described above, any excessively large bubbles are removed and the resulting contrast medium is drawn into a syringe 11 or other container for injection into the patient 20. An intravenous catheter 22 is inserted by a nurse or other qualified technologist into a suitable vessel, normally a vein in the patient's arm. Syringe 11 is then placed on a pump 12 or other type of pressurizing device, with the pump having been programmed for the procedure through a user interface 14. The syringe 11 is then connected to catheter 22 via tubing 18, with the tubing 18 and catheter 22 having been previously filled with saline to eliminate all the air therein to prevent any chance of an air embolism. Once activated and operating according to its programming, the pump 12 injects the contrast medium into the vein. Diluted by the blood, the contrast medium soon passes through the chambers of the right heart, the lungs, the chambers of the left heart, and eventually to the region of interest. During the scanning procedure, the transducer 24 is moved over the region of interest. Processing the reflected ultrasonic waves according to known techniques, the ultrasound imager 26 then produces images of the region of interest on its display screen 26b.

There are several disadvantages inherent to the prior art practices described above. Variations in the preparation process (e.g., mixing, agitation, pressure activation, etc.) can lead to variations in the concentration and size distribution of the microspheres or particles within the contrast medium, which can adversely affect the resulting imaging procedure. There can also be degradation from storage of the delicate powders. After preparation, most contrast agents deteriorate over time, causing the concentration of the microbubbles or particles to decrease and their size to vary with time. Contrast agents in the form of microbubbles are also adversely affected by pressure before or during administration. The gas in the microbubbles tends to diffuse into the carrier liquid. The smaller the microbubble, the greater the pressure it experiences due to surface tension (Laplace pressure) and the faster its gas diffuses into the liquid. Gas can also diffuse into a microbubble, causing it to grow unacceptably large. These problems affect the concentration and the size of the microbubbles within the contrast medium.

Microbubbles are mechanically fragile and thus can be destroyed during both injection and storage. The pressure at which the injections are currently given must be severely limited to prevent destruction of the microbubbles. Because microbubbles are lighter than the liquid carrying them, they tend to rise and separate from the liquid between creation and injection. This leads to non-uniform or even non-diagnostic bubble densities. To overcome this, various methods have been devised for agitating the microbubbles between the time they are created and the moment at which they are injected into the patient. WO 00/53242A1 by Trombley et al) (see also WO 99/27981), incorporated herein by reference, discloses one (or more) such methods of agitation.

Another shortcoming of the prior art practice relates to the limited lifetime of such contrast media and the need for sterile conditions in handling and administration. A contrast medium must be used soon after it is mixed or otherwise prepared. When the imaging procedure requires less contrast media than what a vial provides, the unused portion is routinely discarded, which represents a waste of money. Conversely, when more contrast media is required, a new vial must be mixed in the middle of an imaging procedure. Not only does this prove inconvenient and distracting to the technologist, it takes a significant amount of time, which also translates into increased costs.

In an alternative, U.S. Pat. No. 6,231,513 B1 to Daum et al. teaches an apparatus and method to create carbon dioxide bubbles within the blood vessel being imaged. There is a benefit to using carbon dioxide because the gas has minimal physiological effect. There is also the benefit that the bubbles can be created as needed. There are several difficulties with this method, however. First, access has to be gained to the particular vessel to be imaged, because bubbles of carbon dioxide will not reliably travel through the lungs. Second, there is no way to measure or monitor the number or size distribution of the bubbles being created. Furthermore, as the patent concedes, a wide range of large bubbles is created. If these bubbles were created with any gas other than carbon dioxide, they would represent a significant hazard to the patient, as it would pose a risk of embolization or blockage of vessels and capillaries downstream. Lastly, if there is any failure, large bubbles of $CO_2$ might be created in the blood vessel. Because carbon dioxide dissolves reasonably quickly, the bubbles are not likely to produce serious symptoms or tissue damage. They can, however, disturb the flow of blood and thus disrupt the imaging procedure. Thus, there are significant drawbacks and limitations to the apparatus and method disclosed by Daum et al.

OBJECTIVES OF THE INVENTION

It is, therefore, an objective of the invention to provide a system for creating bubbles on demand for use within a medium that can be injected or otherwise administered to a patient for purposes of a medical procedure.

Another objective is to provide a system for creating a medium of bubbles on demand for administration to a patient for purposes of a medical procedure, such as those used to acquire images of the anatomy or to influence or deliver therapy.

A further objective is to provide a bubble generating apparatus for creating bubbles on demand within a medium that can be injected or otherwise administered to one or more patients for purposes of a medical procedure.

An additional objective is to provide a method of generating a medium of bubbles on demand for administration to a patient for purposes of a medical procedure.

A related objective is to adjust in real time the concentration, composition and/or size of the bubbles or other properties of the medium that is to be administered to a patient.

Another related objective is to create a system and/or method of generating a microbubble contrast medium whose properties can be controlled in a way that facilitates a wide variety of imaging techniques and therapeutic procedures.

Yet another related objective is to provide an apparatus that creates microbubbles on demand within a medium, which is intended for contemporaneous injection into a patient to obtain images of the anatomy or to influence or deliver therapy.

In addition to the objectives and advantages listed above, various other objectives and advantages of the invention will become more readily apparent to persons skilled in the relevant art from a reading of the detailed description section of this document. The other objectives and advantages will become particularly apparent when the detailed description is considered along with the drawings and claims presented herein.

SUMMARY OF THE INVENTION

The foregoing objectives and advantages are attained by the various embodiments and related aspects of the invention summarized below.

In one preferred embodiment, the invention provides a system for creating bubbles on demand for use within a medium administrable to a patient for purposes of a medical procedure. The system comprises a reservoir, a pressurizing device, a bubble generator, and a controller. The reservoir is used to store a liquid. The pressurizing device is used to convey the liquid, and the medium formed therewith, through the system. The bubble generator is used to create the bubbles of gas within the liquid to form the medium. The bubble generator has an inlet for receiving the liquid and an outlet for communication of the medium to the patient. The controller controls the operation of the system so that the bubbles created by the bubble generator are generated according to the demands of the medical procedure and are administrable within the medium to the patient. The invention also provides several bubble generators capable of being used within the system.

In another preferred embodiment, the invention provides a system for creating a medium of bubbles on demand for administration to a patient for purposes of a medical procedure. The system comprises a primary reservoir, an additional reservoir, at least one pressurizing device, a bubble generator, and a controller. The primary reservoir accommodates a first liquid. The additional reservoir accommodates at least one of a second liquid and a gas. The at least one pressurizing device is used to convey the first liquid and at least one of the second liquid and the gas, and the medium formed therewith, through the system. The bubble generator has at least one inlet for receiving the first liquid and at least one of the second liquid and the gas, and creates therefrom the medium. The bubble generator has an outlet for communication of the medium to the patient. The controller controls the operation of the system so that the bubbles created by the bubble generator are generated according to the demands of the medical procedure and administrable within the medium to the patient. The invention also provides several bubble generators capable of being used within the system.

In a related aspect, the invention provides a bubble generating apparatus for creating bubbles on demand within a medium administrable to at least one patient for purposes of a medical procedure. The bubble generating apparatus comprises at least one inlet, a generating mechanism, and an outlet. The at least one inlet is used to receive into the generating mechanism at least one of a first liquid, a second liquid, and a gas. The generating mechanism creates the bubbles to form the medium from at least one of the first liquid, the second liquid, and the gas. The outlet is used to conduct the medium from the bubble generating apparatus to the at least one patient.

The invention also provides a method of generating a medium of bubbles on demand for administration to a patient for purposes of a medical procedure. The method comprises the step of providing a source of at least one of a first liquid, a second liquid and a gas. A subsequent step involves generating the bubbles using at least one of the first liquid, the second liquid, and the gas and creating the medium therewith. The method also includes the step of controlling generation of the bubbles so that the bubbles are generated according to the demands of the medical procedure and are administrable within the medium to the patient.

The invention further provides a system for creating a plurality of differentiable populations of bubbles of gas for use within a medium administrable to a patient for purposes of a medical procedure. The system includes at least one reservoir, at least one pressurizing device, and at least one bubble generator. The at least one reservoir is used to accommodate at least one of a liquid and the gas. The at least one pressurizing device is used to convey at least one of the liquid and the gas, and the medium formed therewith, through the system. The at least one bubble generator has at least one inlet for receiving the liquid and the gas and creates therefrom the plurality of differentiable populations of bubbles. The at least one bubble generator has at least one outlet for communicating the medium, and the plurality of differentiable populations of bubbles therein, to the patient.

BRIEF DESCRIPTION OF THE DRAWINGS

The invention, and particularly its presently preferred and alternative embodiments and related aspects, will be better understood by reference to the detailed disclosure below and to the accompanying drawings, in which:

FIG. 14 illustrates a twelfth embodiment of the bubble generator of FIGS. 2A-2B;

FIG. 15 illustrates a thirteenth embodiment of the bubble generator shown in FIGS. 2A-2B; and FIG. 16 depicts a fourteenth embodiment of the bubble generator of FIGS. 2A-2B.

Figure 1:
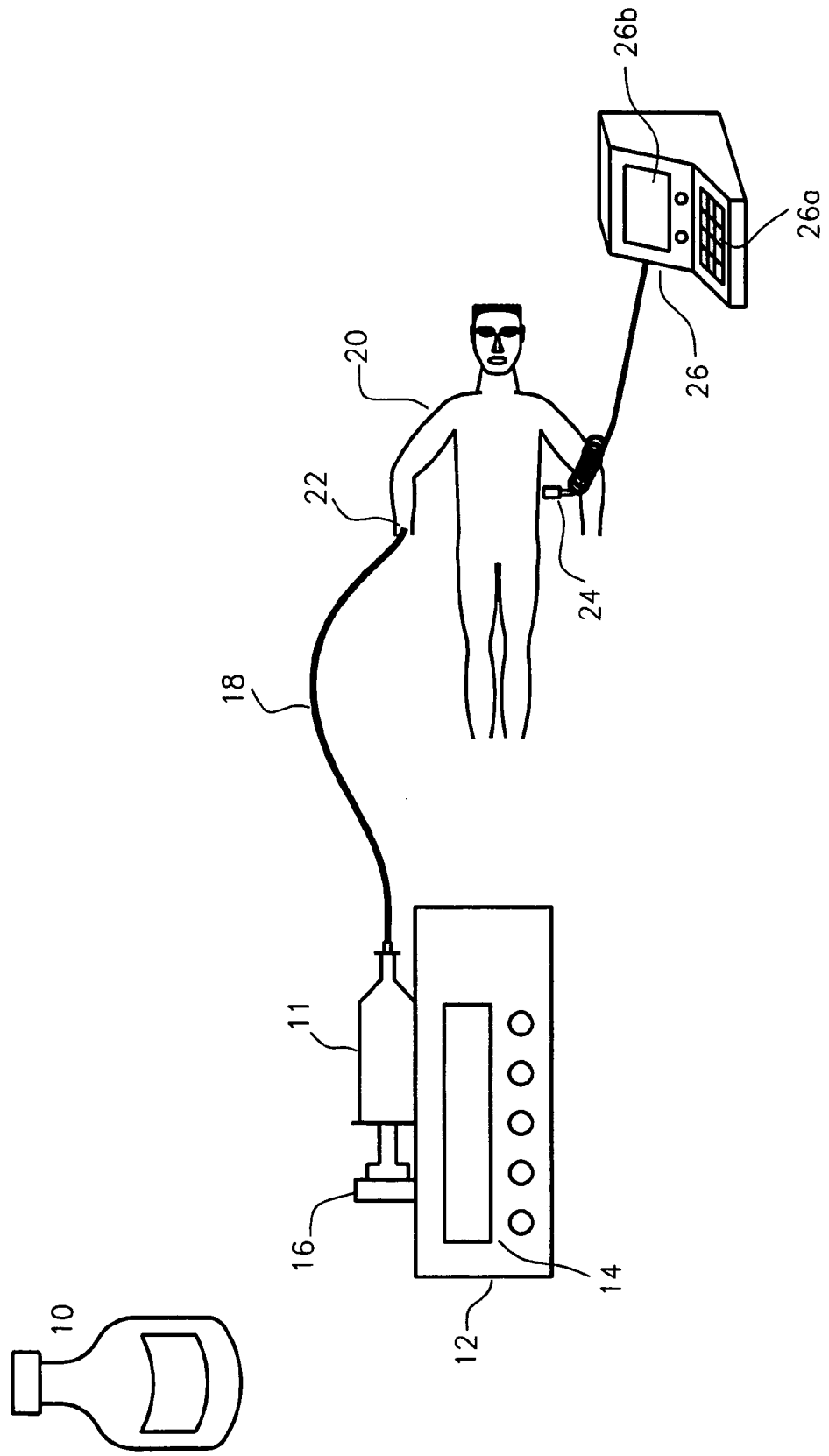
FIG. 1 shows a prior art system for injecting a bubble contrast medium, produced beforehand according to prior art practice, into a patient for obtaining images of the anatomy of the patient during an ultrasound scanning procedure.

DETAILED DESCRIPTION OF THE PRESENTLY PREFERRED AND ALTERNATIVE EMBODIMENTS OF THE INVENTION

Although the various embodiments and related aspects of the invention herein described and illustrated are presented primarily in the context of ultrasound imaging procedures, the reader should understand that the invention may also be applied or adapted to other types of applications such as CT, PET, MRI and MRA procedures as well as a wide variety of therapeutic procedures. The various embodiments and related aspects of the invention will now be described with reference to the accompanying drawings, in which like elements have been designated where possible by the same reference numerals.

Figure 2A:
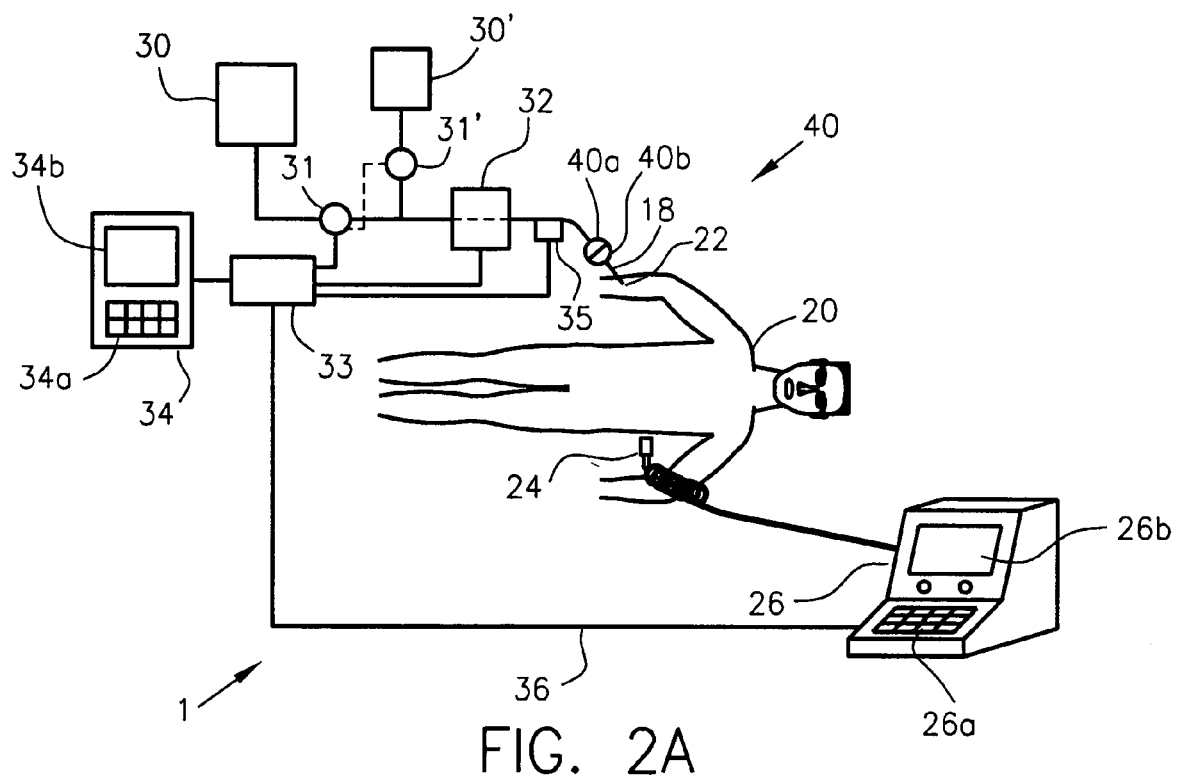
FIG. 2A illustrates a preferred embodiment of a system for injecting a contrast medium, whose microbubbles are produced on demand by a bubble generator, into a patient for obtaining images of the anatomy during an ultrasound scanning procedure.

FIG. 2A illustrates a presently preferred embodiment of a system, generally designated 1, for creating microbubbles on demand for use within a medium administrable to a patient undergoing an imaging procedure. As shown in the context of ultrasound imager 26, the system 1 includes a container 30, a pump 31, a microbubble generator 32, a controller 33 with associated user interface 34, a connector assembly 40, a catheter 22 and associated tubing. Ideally, the novel system 1 also features a fluid monitor or verification device 35. In operation, described simply, the system 1 enables its pump 31 to convey liquid from container 30 to the microbubble generator 32 wherein microbubbles are formed on demand within the liquid. Subject to further processing by the controller 33 and/or the fluid monitor 35 as is explained below, the liquid and the microbubbles it carries is eventually conveyed through tubing to the patient into whom it is injected through the catheter 22, as shown in FIG. 2A.

Referring now to the individual components of system 1, container 30 serves as a storage reservoir primarily to hold the unprocessed, yet sterilized, liquid within which the microbubbles are to be formed according to several of the embodiments described below. Pump 31 can take the form of any one or more of a number of known pressurizing devices, such as a gear pump, a peristaltic pump, or even a syringe pump. Alternatively, the container 30 itself may be used as the pump, as it could be pressurized to provide the pumping force required by the system. Another, perhaps simpler, alternative to pump 31 would be to exploit gravity to create the fluid flow for the system 1 shown in FIG. 2A.

The microbubble generator of the invention can be manifested in any one or more of several embodiments, each of which is described below in detail. The invention contemplates at least five broad categories or classes of microbubble generator. In a first class of microbubble generator, the microbubbles are created by disrupting a liquid in the presence of a gas. A second class of microbubble generator uses a liquid supersaturated with a gas along with nucleation sites or materials to create the microbubbles and/or two liquids that, when combined, create the microbubbles in the presence of such nucleation sites or materials. A third class uses cavitation to create microbubbles within a liquid. A fourth class produces microbubbles by entraining or otherwise introducing a gas into a flow of liquid in such a way to form microbubbles of the proper size. A fifth class generates microbubbles using two dissimilar liquids and/or two such liquids and a gas.

Controller 33 of the invention allows an operator to govern the overall operation of system 1. Its user interface 34 preferably features a keyboard 34a and a display screen 34b with which the operator can visually monitor and even change the various operating parameters of the system. For example, through its user interface 34, controller 33 enables the operator to operate pump 31 and generator 32 so as to select the optimum rate at which the microbubble contrast media should flow for the particular imaging procedure being performed. Furthermore, through a communications link 36 with ultrasound imager 26, the controller 33 can provide real time adjustment of microbubble generation or delivery parameters such as the flow rate and size of the microbubbles, their chemical composition and their stiffness, with the goal of stabilizing and/or optimizing the image or diagnostic information obtained during the scanning procedure. This is discussed in detail in U.S. application Ser. No. 09/300,326, filed Apr. 27, 1999, which was granted May 28, 2002, as U.S. Pat. No. 6,397,098, which is incorporated herein by reference.

Preferably disposed between generator 32 and connector assembly 40, fluid monitor 35 may be used to perform several functions, and may be manifested as one or several discrete packages of equipment. Its primary function could be gross gas detection by which it would detect the presence of large amounts of gas in the fluid path and prevent injection of same into the patient 20. More generally, fluid monitor 35 could at least complement, if not perform by itself, some of the functions performed by controller 33 via feedback from ultrasound imager 26. Specifically, it could be used to monitor one or more properties of the microbubbles and provide real time adjustment of various parameters pertaining to generation and/or delivery of the microbubbles for the purpose of stabilizing and/or optimizing the image or diagnostic information. Examples of the properties that could be monitored include the size, flow rate, chemical composition and stiffness of the microbubbles. In particular, fluid monitor 35 could monitor the size and/or density of the microbubbles to determine whether bubble generator 32 is operating as expected. It could also monitor the foregoing parameters and then selectively destroy microbubbles as described in U.S. Pat. No. 6,317,623 B1 to Griffiths et al, cited above.

The system 1 of the invention may also feature an auxiliary container 30' as an addition to primary container 30 discussed above. As shown in FIG. 2A, this auxiliary container 30' is also connected to the fluid path upstream of microbubble generator 32 via an auxiliary pump 31'. In lieu of the auxiliary pump, the primary pump 31 can be made so that its inlet is rendered switchable between the primary and auxiliary containers 30 and 30'. Should the system be deployed without auxiliary container 30', the operator would typically use the liquid in the primary container 30, within which the microbubbles are to be formed, to prime the entire fluid path, as such priming is necessary in such systems to prevent air embolisms. Contrast media is expensive, however. Consequently, by using auxiliary container 30' and filing it with another liquid (e.g., saline), the fluid path can be primed at relatively low cost, yet still safely. For use in relation to flushing or pre-filling, container 30' may be connected elsewhere in the fluid path, for example downstream of bubble generator 32 or fluid monitor 35. Moreover, rather than flushing or pre-filling liquids, the auxiliary container 30' could contain a liquid or a gas that is integral to the process of bubble generation. In this case, the controller 33 would then be used to control the ratio of the liquid(s)/gas that are pumped from the primary and auxiliary containers 30 and 30' and ultimately sent to microbubble generator 32. Microbubble generators of the type that use two liquids, or a liquid in combination with a gas, to produce the microbubble contrast media are described below.

Given that containers 30 and 30' can be manifested in a variety of sizes and thus hold a large volume of liquid, the system 1 of the invention ought to accommodate a plurality, or succession, of patients. For that reason, connector assembly 40 will preferably feature both reusable and disposable components. These components will collectively prevent system 1 as a whole, and the reusable components in particular, from being contaminated by any one or more patients. Many ways of preventing contamination in systems capable of accommodating multiple patients are described in U.S. Pat. Nos. 5,569,181, 5,739,508, 5,806,519, 5,840,026, 5,843,037, 6,149,627 and 6,306,117, which are incorporated herein by reference. For example, connector assembly 40 can include two parts: a reusable element 40a and one or more disposable elements, or per patient hookups, 40b. This design prevents backflow of bodily fluids into the reusable element 40a, and thereby not only prevents contamination of the reusable parts of system 1 but also protects the patients connected to system 1 from any such contamination. Each disposable element 40b is thus intended for use by a single patient, and should therefore be discarded after use. After flowing through connector assembly 40, the liquid and the microbubbles it carries goes through an optional connector tube 18 through catheter 22 then into a vein or other vessel of patient 20. This downstream componentry should also be discarded after use.

Figure 2B:
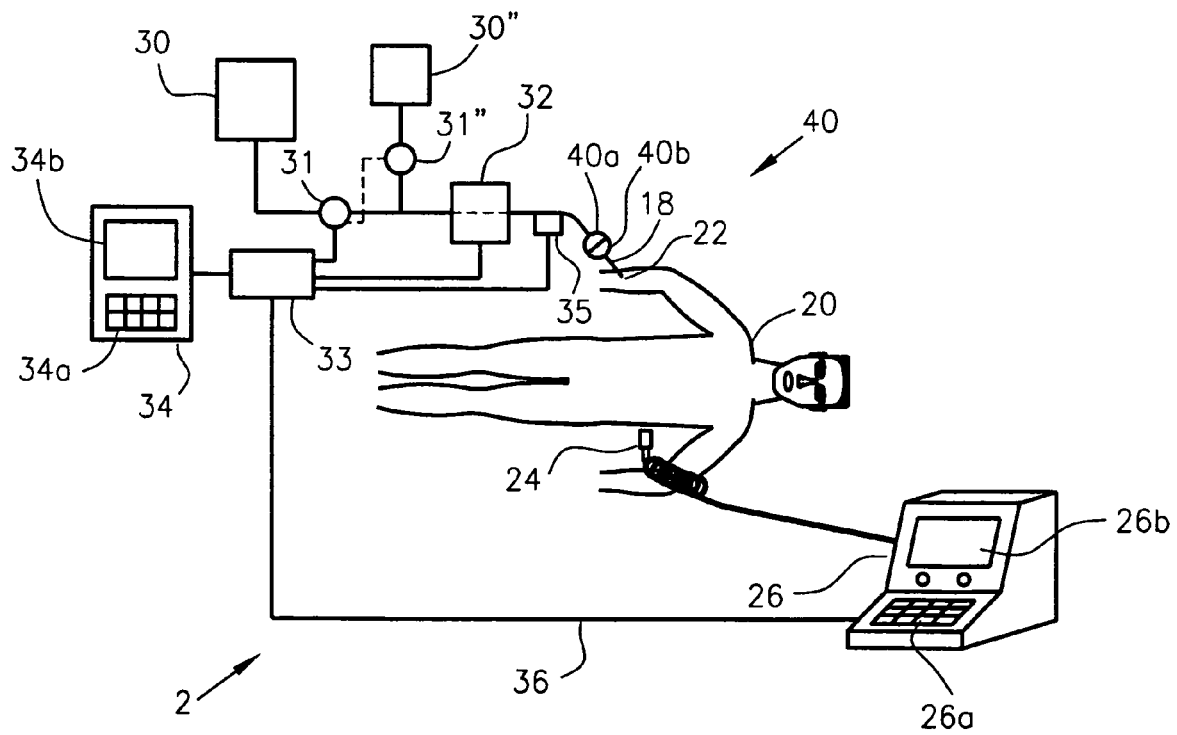
FIG. 2B illustrates an alternative preferred embodiment of a system for injecting a contrast medium, whose microbubbles are produced on demand by a bubble generator, into a patient for obtaining images of the anatomy during an ultrasound procedure.

FIG. 2B illustrates an alternative preferred embodiment of a system, generally designated 2, for creating microbubbles on demand for use as contrast media during an imaging procedure. It is essentially a modification of the system shown in FIG. 2A. As shown in the context of ultrasound imager 26, the system 2 includes the primary container 30, the primary pump 31, the microbubble generator 32, the controller 33 and its user interface 34, the connector assembly 40, and the catheter 22. It also preferably includes fluid monitor 35. This alternative system 2 also features a secondary container 30" and a secondary pump 31" as additions to primary container 30 and primary pump 31. Unlike the auxiliary container and pump of the embodiment shown in FIG. 2A, the secondary container 31" is preferably connected directly to microbubble generator 32, or indirectly through the secondary pump 31".

As mentioned earlier, the microbubble generators disclosed herein use either two liquids, a liquid and a gas, two liquids and a gas, or other combinations thereof, to produce the microbubble contrast media. Consequently, the system 2 may use secondary container 30" as a reservoir for either a liquid or a gas. In fact, system 2 can be adapted to include as many reservoirs and pumps as are needed to produce whatever type of microbubble contrast medium that may be required for any particular imaging procedure. In such an adaptation, the controller 33 will preferably be programmed to provide the operator with a menu of microbubble contrast media from which to choose through user interface 34. More specifically, for any given imaging or therapeutic procedure, the operator could select, for example, the chemical composition of the medium and the specific size of the microbubbles. The system 2 will preferably enable the operator to add targeting chemicals to the bubble shell or wall material, so that, for example, the microbubbles will attach themselves to specific tumors, blood clots, inflammation, or arterial plaques. As compared to prior art practice, novel system 2, if configured as described, will significantly reduce the work of the operator in preparing for imaging and therapeutic procedures and related studies.

The respective systems illustrated in FIGS. 2A and 2B each employ a specific order of components, e.g., a reservoir followed by a pump, a microbubble generator and then by other fluid path elements. These arrangements of components are merely exemplary. As alluded to above, the force with which the fluid is conveyed through the system may be generated by pressurizing the containers 30, 30' and 30" rather than by using their respective pumps 31, 31' and 31". Alternatively, the pumps 31, 31' and 31" may be incorporated into the fluid path downstream, as opposed to upstream, of the microbubble generator. Another alternative would be not to use a pump for one or more of the fluids. For example, gravity or osmotic pressure can be exploited to create the force necessary to propel the fluid(s) downstream. Capillary action, a property taken advantage of in some Inkjet printer cartridges, could also be used to provide the fluid motion.

In addition, the components illustrated in FIGS. 2A and 2B are shown as discrete elements for clarity of understanding. In terms of both manufacturing and use, however, there are advantages to having more integrated elements. An example in a different art is the printer cartridge for the Cannon™ BC-20 Inkjet Printer. In one easy to install package, the printer cartridge contains the reservoir (for the ink), the capillary tubes (to act as the pump), and the generator (to spray/generate the droplets of ink).

Furthermore, in the systems of FIGS. 2A and 2B, the microbubble generators are each at positive pressure relative to the downstream components, and particularly the patient 20. The illustrated systems 1 and 2 thus push the fluid through microbubble generator 32. The microbubbles generated therefore expand slightly as they flow down the pressure gradient and eventually into the patient. It is possible, however, to arrange the components so that the microbubble generator lies at a reduced pressure with respect to the patient or the outside atmosphere. In an alternative configuration (not shown), this can be accomplished by having a pump pull fluid from the microbubble generator. The benefit here is that it is often easier to create larger microbubbles, which upon shrinking will have the desired diameter as they are injected into the patient via catheter 22. Another method of creating large microbubbles that will subsequently shrink is to employ a gas mixture in which one of the gasses (e.g., carbon dioxide) quickly dissolves in the liquid and the other gas (e.g., a perfluorocarbon) does not. If the mixture contains 90% dissolving gas and 10% non-dissolving gas, the volume of each microbubble will shrink 90% because the dissolving gas will dissolve into the liquid carrier.

In yet another possible alternative configuration (not shown), the microbubble generator could feed into an accumulator or reservoir. There are currently two modes of injection of contrast: steady state and bolus. In the steady state (or infusion) mode of injection, it is desirable to have a low but constant rate of injection of microbubbles (typically $10^6$ to $10^9$ microbubbles per ml and a few ml/min injection rate). In the bolus mode of injection, the rate of injection is higher (typically $10^6$ to $10^9$ microbubbles per ml at 1-3 ml/sec injection rate), which is an order of magnitude or more greater than the steady state rate. The bolus quickly establishes a high concentration of microbubbles in the blood stream so that the imaging procedure can start with minimal delay. Because of the limitations of some specific bubble generators, it may not be possible to generate microbubbles at both the desired steady state rate and the bolus rate. Therefore, it is advantageous to accumulate microbubbles over some reasonable time period for injection as a bolus. Some of the microbubble generators disclosed herein incorporate a fluid volume that could serve this function of accumulation. Others will require an external accumulator (not shown).

The systems of FIGS. 2A and 2B also provide several options as to the number of patients that they can accommodate. As disclosed above, each system requires relatively few of its components to be disposed of on a per patient basis, e.g., disposable element 40b, connector tube 18 and catheter 22. The microbubble generator 32, container 30/30'/30" and pump 31/31'/31" can be used for a plurality of patients. These components are preferably disposed of on a less frequent basis, such as when the container(s) are emptied or at the end of a day. This minimizes the chance that some contamination could grow overnight. Alternatively, the microbubble generator could also be disposed of on a per patient basis. Given that several of the microbubble generators disclosed herein feature relatively small elements and/or internal channels, they could become inoperative or blocked if they sit unused for some length of time. An alternative would be to discard both the container(s) and the microbubble generator after use with one patient. This alternative provides not only the greatest protection against cross-contamination but also the greatest guarantee of functionality. A further alternative would be to incorporate cleaning elements within each of the disclosed systems 1 and 2 to sterilize the microbubble generator and selected fluid path elements. Such a design, however, would entail considerable complexity. Other components, such as controller 33 and user interface 34, are preferably made reusable, as they can last for many months or even years. As technology advances, however, these components may become less expensive and eventually disposable. Another alternative would be to use the whole system on one or several patients and then return it in its entirety to the vendor for cleaning and refurbishment. The benefit of this alternative is that the user will always have a "new" system. An analogy to this is the "disposable" camera in which the film is removed and all or parts of the camera can be reused.

The disclosed systems 1 and 2 have several advantages over the prior art practice of providing microbubble contrast media. First, and perhaps most obvious, the operator no longer has to spend time manually mixing and/or re-suspending the microbubbles at the beginning of the procedure. Second, the two systems each allow the operator to prime the fluid path quite easily, whether through a single container using the contrast carrier liquid or a separate container (e.g., auxiliary container 30' or secondary container 30") using a less expensive liquid such as saline. This is true whether the system is configured with a pump having a dual inlet to accommodate both the saline and contrast carrier liquids or with multiple pumps each of which is dedicated to one of the liquids. This will save the operator considerable time in setting up and operating the system. Third, few, if any, microbubbles will be wasted in the fluid path. When the generation of microbubbles is stopped, the fluid flow can be stopped if desired, or the fluid flow can continue to push whatever microbubbles remain in the fluid path into the patient. Fourth, the disclosed systems 1 and 2 allow the microbubbles to be made on demand as needed by the imaging or therapeutic procedure. Due to the configuration of each system, there will be no need to stop a procedure and separately create more microbubbles and reload a dispenser, which would be the case with the prior art systems. Fifth, the microbubbles do not need to pass through a pumping mechanism, which eliminates one potential cause of damage to the microbubbles. If advantageous for other reasons, however, the pump mechanism can be placed downstream of the microbubble generator.

Before discussing the various embodiments of microbubble generator 32 contemplated by the invention, it is appropriate to discuss the properties of the liquid(s) used to create, maintain, and/or deliver the microbubbles. Typically, the liquid will be mostly water. It will also usually contain a surfactant to contain the microbubbles. The surfactant can be composed of proteins, fatty acids, lipids, synthetic materials or a combination thereof. The surfactant serves to stabilize the microbubbles, and can be selected to minimize clumping or agglomeration and to reduce the likelihood of the microbubbles adhering to the walls of the fluid paths. In some situations, the microbubbles are created on the side or surface of a solid particle (e.g., galactose in the case of Levovist™ by Schering AG).

A good summary of the chemistry of contrast materials is contained in U.S. Pat. No. 5,605,673 to Schutt et al., cited above, and in *Ultrasound Contrast Agents*, edited by Barry B. Goldberg, Martin Dunitz Ltd., 1997, incorporated herein by reference. The contrast materials discussed in these references are prepared at one time for one patient, generally as shown in FIG. 1. The chemical and microbubble stabilization properties taught in these references can be used in association with the microbubble on demand generator apparatuses and systems disclosed in this document. Because of the wide variety in liquid and surfactant properties, the specifics of the liquid solvent and solutes involved will determine some of the features of the microbubble generator(s). The options are too numerous to cover all possibilities in detail in this disclosure. This disclosure gives sufficient detail that someone knowledgeable about the various contrast media properties could successfully create microbubbles as needed.

The terms "vapor" and "gas" are used herein interchangeably. Similarly, when referring to the tension of a dissolved gas in a liquid, the more familiar term "pressure" may be used interchangeably with "tension." "Gas osmotic pressure" can be thought of as the difference between the partial pressure of a gas inside a microbubble and the pressure or tension of that gas (either in a gas phase or dissolved in a liquid phase) outside of the microbubble, when the microbubble membrane is permeable to the gas. More precisely, it relates to differences in gas diffusion rates across a membrane. The term "membrane" is used to refer to the material surrounding or defining a microbubble, whether it be a surfactant, another film-forming liquid, or a film-forming solid or semisolid. "Microbubbles" are generally considered as microbubbles when they have a diameter between about 0.5 and 300 µm, preferably having a diameter no more than about 200, 100, or 50 µm. For transpulmonary use, the microbubbles have a diameter preferably not more than about 10 to 3 µm (measured as average number weighted diameter of the microbubble composition). When referring to a "gas," it will be understood that mixtures of gases together having the requisite property fall within the definition, except where the context otherwise requires. Thus, in this disclosure, air may typically be considered a gas.

Figure 3:
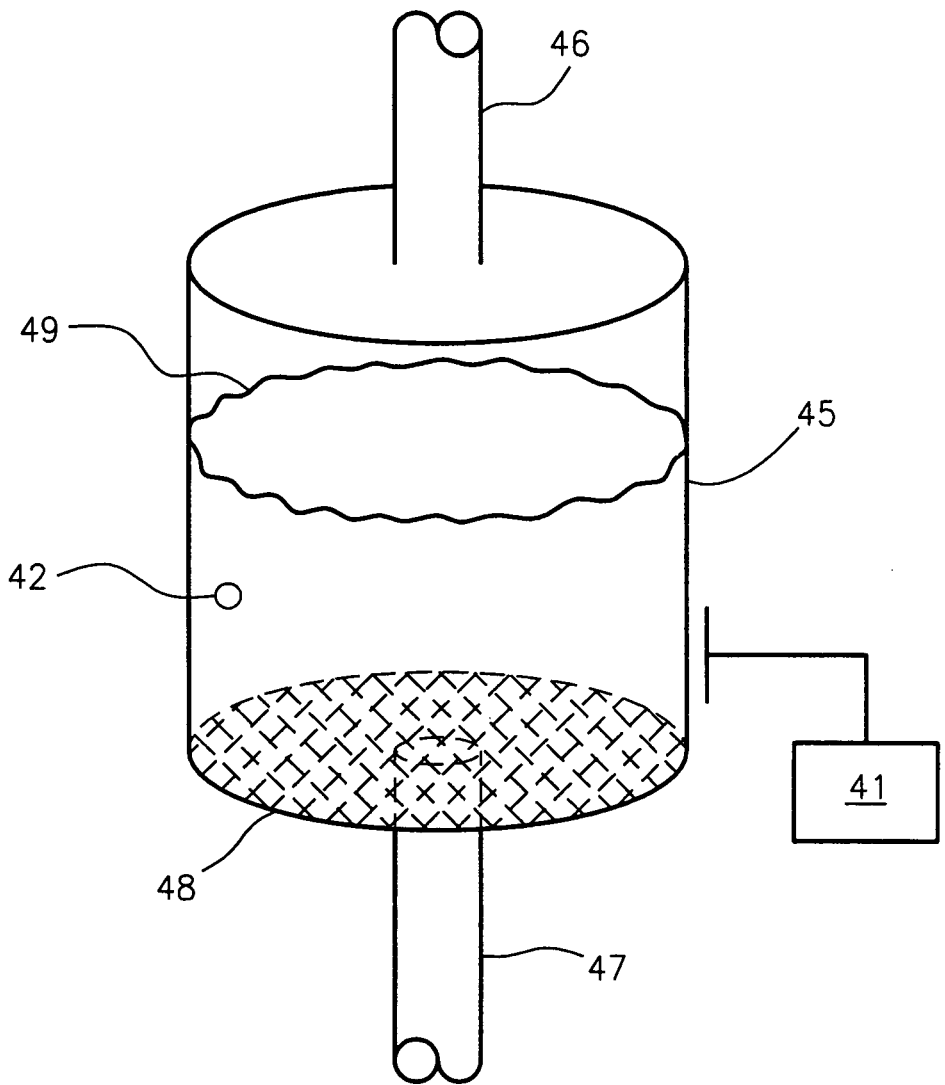
FIG. 3 illustrates one embodiment of the bubble generator shown in FIGS. 2A-2B.

FIG. 3 illustrates a first embodiment of the microbubble generator, one capable of generating microbubbles on demand when incorporated within the disclosed systems 1 and 2. It employs a gas-liquid interface and a means of disrupting that interface to create microbubbles of the desired diameter. More specifically, the microbubble generator includes an enclosure 45, a mechanism 41 for agitating the enclosure, two fluid path conduits 46 and 47 and, preferably, a filter 48. Designed to withstand the forces associated with vigorous shaking, the enclosure 45 is the container within which to agitate the liquid in the presence of a gas. The agitating mechanism 41 can be manifested in any number of ways, such as something akin to a dental amalgam mixer. Fluid path conduits 46 and 47 are preferably made from a flexible material. They should possess a degree of flexibility sufficient to permit container 45 to be shaken during normal operation without suffering any damage to either itself or its associated fluid path conduits. Filter 48 may take several forms, including a membrane with small holes, a fine mesh, or a sintered material.

Operating within system 1, for example, this microbubble generator allows liquid to flow from pump 31 through inlet conduit 46 and into container 45 where it is shaken. In particular, the agitating mechanism 41 responds to a control signal from controller 33 by shaking the container 45, thereby agitating the interface between the liquid and the gas. Placing one or more metal or ceramic balls 42 within container 45 could further improve the mixing action. The shaken mixture is then directed to filter 48, which removes any microbubbles that have a diameter greater than a predetermined minimum. The resultant solution then exits container 45 through outlet conduit 47 from which it is to be conveyed to the patient via connector assembly 40, tubing 18 and catheter 22.

In lieu of a simple membrane or mesh filter, filter 48 may be implemented as an active filtering system. It could take the form of centrifugal separation, buoyancy sieve or separation, ultrasonic-activated microbubble destructions, ultrasonic separation using Bjerkness forces, or electric field or current-induced separation. The optimum filtering system could include two or more different mechanisms to optimize the distribution based on microbubble size. It would select out microbubbles greater than one specific diameter and also microbubbles smaller than a second specific diameter.

The gas in container 45 can be air or some other suitable gas, such as those discussed above or those revealed in various prior art references. If the quantity of microbubbles being generated within container 45 uses relatively little volume, the gas could come prepackaged within the microbubble generator itself. If, however, the quantity of gas used is significant compared to the size of container 45, then auxiliary container 30' and pump 31' could supply gas to make up for that which leaves in the microbubbles. Alternatively, the microbubble generator could be constructed with an additional conduit though which container 45 could be resupplied from auxiliary container 30' with gas during use, between successive uses, or when otherwise needed.

Figure 4A:
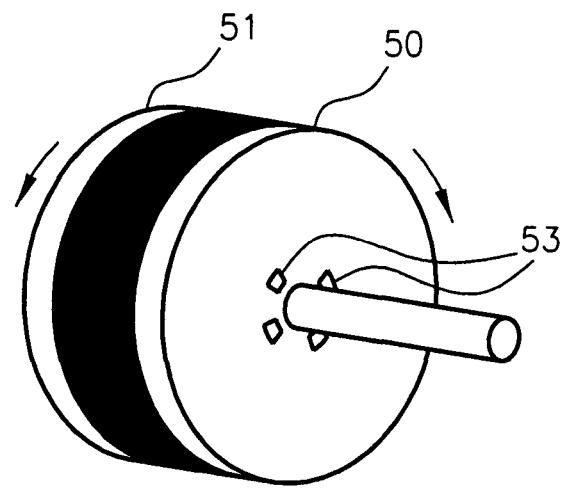
FIGS. 4A and 4B illustrate a second embodiment of the bubble generator shown in FIGS. 2A-2B.
Figure 4B:
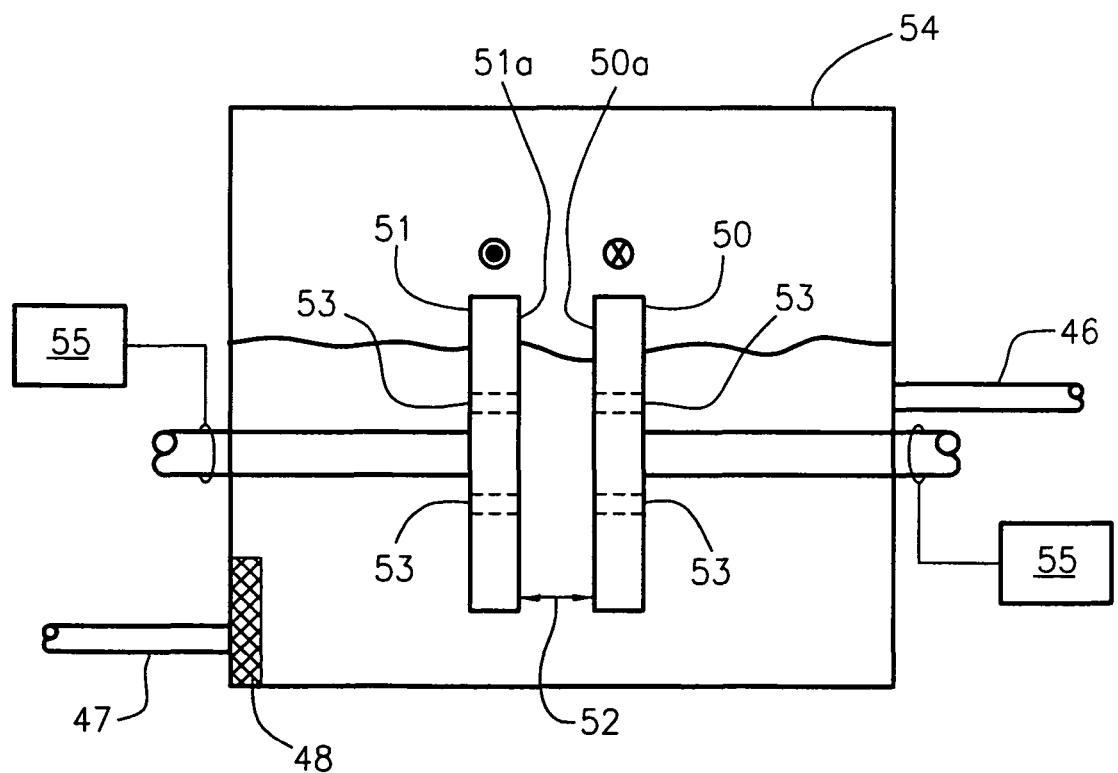

FIGS. 4A and 4B illustrate a second embodiment of the microbubble generator. Like the embodiment of FIG. 3, this embodiment employs a gas-liquid interface and a means of disrupting that interface to create microbubbles of the desired diameter. More specifically, the microbubble generator includes an enclosure 54, two disks 50 and 51, a mechanism 55 for spinning the disks, two fluid path conduits 46 and 47 and, optionally, a filter 48. Enclosure 54 is the container within which the liquid is disturbed in the presence of the gas. Situated within the enclosure, disks 50 and 51 are separated by a gap 52 of a preset thickness and are capable of being spun in opposite directions. Each disk has an inlet hole 53 proximate its center and a rough surface on its inwardly facing side. As best shown in FIG. 4B, gap 52 between the rough surfaces 50a and 51a is preferably 1 mm or less. Situated near the outlet conduit 47, filter 48 can be implemented in any of the ways described in connection with the first embodiment, including active filtering.

When incorporated within system 1, for example, this microbubble generator allows liquid to flow from pump 31 through inlet conduit 46 and into container 54. In response to a control signal from controller 33, mechanism 55 reacts by spinning the two disks 50 and 51. The rough surfaces 50a and 51a on the inwardly facing sides of the disks serve to pull the gas into the liquid, creating microbubbles as they spin. More specifically, because the disks rotate in opposite directions, the net liquid level contained between them for moderate speeds of rotation is approximately what it would be were the disks not spinning. The inlet holes 53 near the center of the disks allow liquid to enter gap 52 between the disks because, as the disks spin, they exert a net outward flow to the liquid. This carries the entrained microbubbles out of the space between the disks 50 and 51. The resulting microbubble contrast medium is then directed to filter 48, which ensures that only microbubbles with the desired size distribution exit the container 54. The resultant solution then exits container 54 through outlet conduit 47 from which it is to be conveyed to the patient via connector assembly 40, tubing 18 and catheter 22.

Disks 50 and 51 can be operated in two different modes. In the "slow mode," the microbubbles are created by air trapped on the rough surfaces 50a/51a of the disks as those surfaces are brought into the liquid. These microbubbles are subsequently dislodged by the relative flow of the liquid over those rough surfaces upon submersion. In this mode, the separation of the disks is not critical, and additional means such as a jet of fluid directed at the rough surfaces 50a/51a of the disks could be applied to dislodge the microbubbles. In the "fast mode," sufficient turbulence is created at the gas-liquid interface that microbubbles are created by the turbulence rather than by the topological details of the surfaces. The surface of each disk primarily imparts mechanical energy to the gas-liquid interface rather than assisting in the creation of individual microbubbles.

The counter-rotation disks 50 and 51 and spinning mechanism 55 together essentially serve as a means for agitating the liquid so as to make the invention operate in the previously described manner. Various other arrangements of these parts or even different parts that together perform the same function as the cited means are intended to be encompassed by one or more of the claims presented below.

Figure 5A:
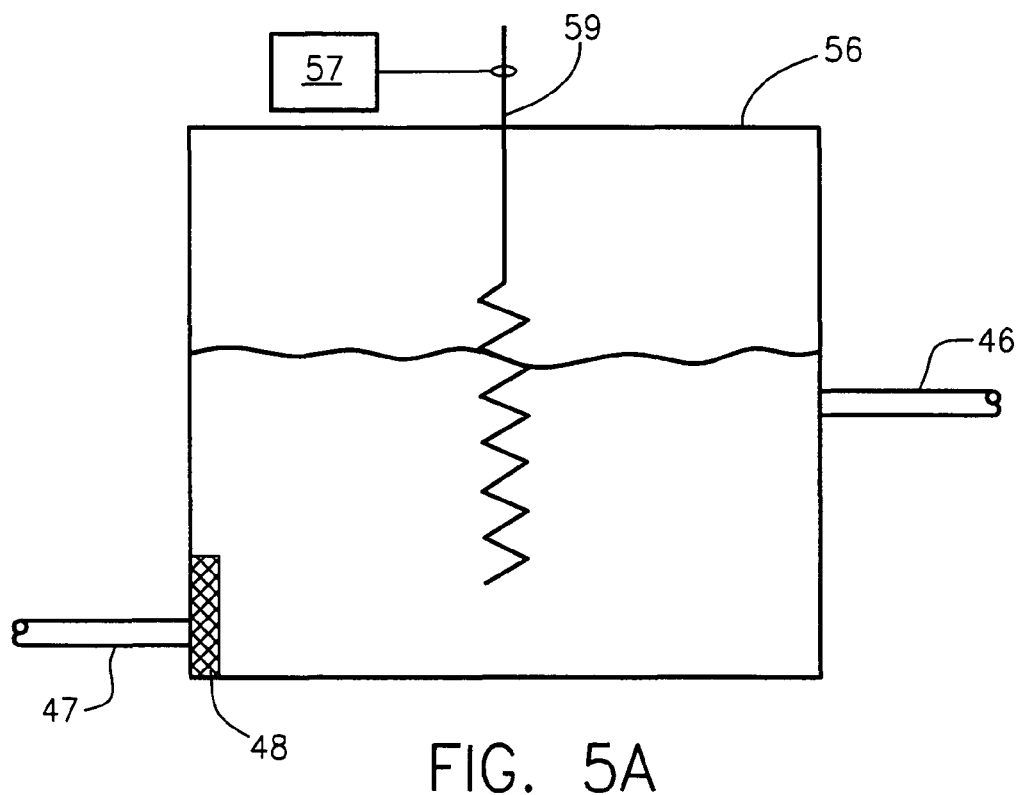
FIG. 5A depicts a third embodiment of the bubble generator of FIGS. 2A-2B.
Figure 5B:
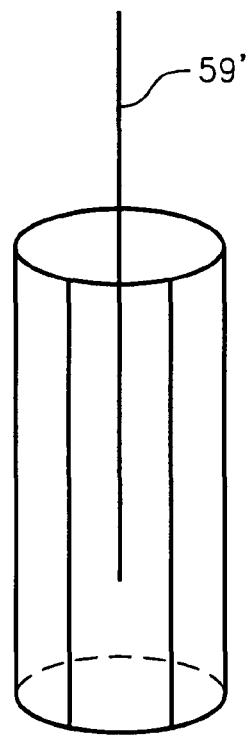
FIG. 5B illustrates an alternative to the stirring element shown in FIG. 5A.

FIGS. 5A and 5B illustrate a third embodiment of the microbubble generator. It too employs a gas-liquid interface and a means of disrupting that interface to create microbubbles of the appropriate diameter. More specifically, the microbubble generator includes an enclosure 56, a stirring element 59, a mechanism 57 for rotating the stirring element, two fluid path conduits 46 and 47 and, preferably, a filter 48. Enclosure 56 is the container in which the interaction between the liquid and gas takes place. Situated within enclosure, stirring element 59 is preferably submerged only partially in the liquid. Situated near the outlet conduit 47, filter 48 can again be implemented in any of the ways described in connection with the previous embodiments, including active filtering.

Stirring element 59 can be implemented as a partially coiled wire loop, a whisk or various other beating elements. For example, as shown in FIG. 5B, the stirring element may be composed of multiple small wires, as denoted by reference numeral 59', rather than the single helix loop shown in FIG. 5A. This variation of stirring element would yield a significant increase in the number of microbubbles created by the microbubble generator.

Incorporated within system 1, this microbubble generator would, in operation, allow liquid to flow from pump 31 through inlet conduit 46 and into the enclosure 56. In response to a control signal from controller 33, the rotating mechanism 57 would react by rotating the stirring element 59/59'. At the point where the stirring element cuts through the surface of the liquid, microbubbles would be created. The resulting mixture would then be directed to the filter 48, which ensures that only microbubbles with the desired size distribution exit the enclosure. The resulting microbubble contrast medium would then exit enclosure 56 through outlet conduit 47 from which it is to be conveyed to the patient via connector assembly 40, tubing 18 and catheter 22.

To create the microbubbles even more readily, the gas used can be a mixture with a high percentage of carbon dioxide. As discussed in U.S. Pat. No. 5,605,673, carbon dioxide has a strong tendency to quickly leave the microbubbles and dissolve back into the liquid, thus causing the microbubbles to shrink significantly. There are other gases with operational characteristics similar to carbon dioxide in this regard.

An additional mechanism to disrupt the gas-liquid interface is to have a high speed flow of liquid (or gas) impinge on the gas-liquid interface. This high speed flow could be introduced through inlet conduit 46 and thus from the flow of the liquid medium itself. Alternatively, there could be a pump that pulls some of the gas or liquid from the microbubble generator. In this scenario, the pump would then pressurize it and reintroduce it into the enclosure 56 so that it impinges on the gas-liquid interface.

It should be apparent that stirring element 59 and rotating mechanism 57 basically function as a means for agitating the liquid so as to make the invention operate in the previously described manner. Various other arrangements of these parts or even different parts that together perform the same function as the cited means are intended to be encompassed by one or more of the following claims.

Figure 6:
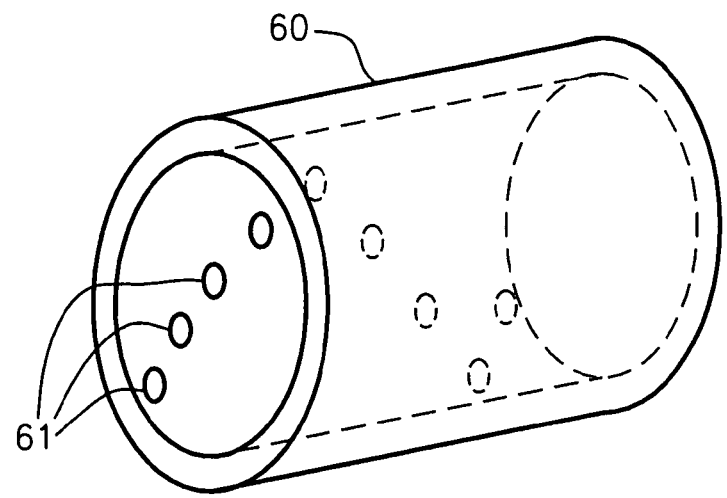
FIG. 6 illustrates a fourth embodiment of the bubble generator of FIGS. 2A-2B.
Figure 7:
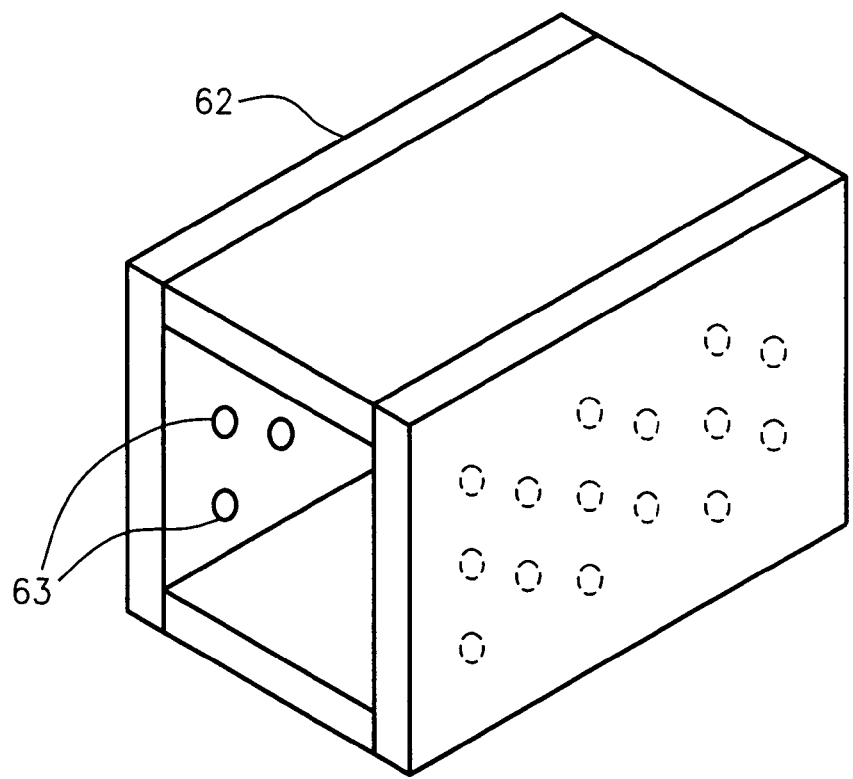
FIG. 7 illustrates a fifth embodiment of the bubble generator of FIGS. 2A-2B.

FIGS. 6 and 7 illustrate a second class of microbubble generator, one in which the bubbles are created using a liquid that is supersaturated with a gas. Depending on the exact type of generator being discussed, the liquid in which the gas is dissolved may or may not contain nucleation materials. The gas can be any of the ones currently used. Air is a good choice, as is nitrogen. To prepare the contrast medium, the gas is dissolved into the liquid under pressure. It can either come prepackaged under pressure or be pressurized in the primary container 30 shown in FIG. 2A or 2B.

FIG. 6 depicts the essential details of a fourth embodiment of microbubble generator, one built to operate as part of the disclosed systems 1 and 2. More specifically, this microbubble generator includes a passage or nozzle 60 or an array of such nozzles. Preferably cylindrical in shape, the nozzle 60 features a plurality of nucleation sites. Each nucleation site 61 can take the form of a pit several microns in diameter, preferably on the order of 3 to 100 μm. Each pit is formed in the inner wall of the nozzle 60, and would ideally be deep enough and of a profile such that the liquid does not wet down to the bottom during normal handling and preparation. Several alternative geometries are possible. Instead of a planned arrangement or layout of pits, the pattern of pits could be randomized.

Equipped with a microbubble generator of the type shown in FIG. 6, the systems of FIGS. 2A and 2B would operate generally as follows. In response to a control signal from controller 33, the pump 31 would cause the liquid in the primary container 30 to flow into the nozzle. The nozzle 60 would channel the liquid from left to right, as viewed from the perspective of FIG. 6. As the liquid moves through the nozzle or tube, the pressure decreases, and the liquid becomes supersaturated with the gas. As this supersaturated solution flows over a nucleation site 61, the gas comes out of solution at which point the microbubbles grow. Specifically, at each nucleation site 61, when a microbubble gets large enough, the force of the flow dislodges it and entrains it in the flow of the liquid, and a new microbubble can start to grow. The force on a bubble and thus the size of the bubble created is a function of the flow rate and viscosity of the liquid.

A fifth embodiment, also assignable to this second class of microbubble generator, can be constructed as shown in FIG. 7. This microbubble generator has a nozzle 62 formed from flat plates 64 attached together to form a pipe or passage with a rectangular cross-section. Pits are formed on one side of the flat plates 64 so that the inner walls of the pipe provide the requisite nucleation sites 63. This geometry would be particularly advantageous because technology similar to that used to manufacture compact discs could be employed to fabricate the flat plates 64 with tiny pits on their surfaces. This would simplify construction, as the nozzle 62 could be made by mere assembly of the flat plates 64. Alternatively, the nozzle/passage 62 could be made from two identical L-shaped members to simplifying molding and gluing of the assembly.

In both versions, at least one of the inner walls of the rectangular pipe should be pitted, as such pits serve as the nucleation sites 63 at which the microbubbles will form.

For either of the two embodiments in this second class of microbubble generator, the liquid can be kept under pressure until it enters the microbubble generator. As the liquid travels through or exits the nozzle, the pressure will then decrease. If the liquid itself contains particles or chemicals that act as nucleation sites (in which case the pits 63 would not necessarily be needed), the gas will come out of solution and thereby create the microbubbles. The size of the microbubbles are influenced by many factors including, for example, the amount of gas dissolved in the liquid, the solubility of the gas in the liquid, the density of nucleation sites or particles, the velocity at which the liquid exits the nozzle, the turbulence of the fluid flow or lack thereof, and the temperature of the liquid. By "nozzle" is meant any fluid path conduit that has a sufficient drop in pressure across it so that the gas becomes supersaturated in the liquid as the pressure decreases. Another term that could be used is a flow restriction. If the amount of gas dissolved in the liquid within container 30 is sufficient, the overpressure could be sufficient to drive the liquid through the nozzle.

An alternative to pressurizing the liquid in the container 30/30' is to operate or place the microbubble generator at a reduced pressure with respect to the container and/or the external atmosphere. Thus, although the liquid in which the gas is dissolved will not be supersaturated at atmospheric pressure, it will be supersaturated when it is introduced to the reduced pressure within the microbubble generator. In response to the reduced pressure, microbubbles will form at the nucleation sites. The second benefit with this sub-atmospheric approach, as alluded to above, is that the microbubbles shrink as they are subsequently pressurized and delivered to the patient. Microbubbles of the desired size can thus be created in a controlled fashion by either controllably releasing the pressure or controllably providing the nucleation sites.

As a variation on the embodiments shown in FIGS. 6 and 7, it is also possible to use two liquids with chemical properties such that, when combined, they react to produce a chemical that prefers to be a gas at the temperatures and pressures involved. One example involves using sodium bicarbonate ($NaHCO_3$) and hydrochloric acid (HCl) dissolved in water. When combined, those chemicals produce sodium chloride (NaCl), water ($H_2O$), and carbon dioxide ($CO_2$), which are all physiologically innocuous in small quantities. For this to be accomplished, two liquids shall be used, as represented by containers 30 and 30" in FIG. 2B. This ensures that the reaction occurs in the microbubble generator with sites for the nucleation of the microbubbles. The microbubbles can be nucleated by particles or chemicals in either liquid or by features related to the microbubble generator as discussed above in relation to FIGS. 6 and 7.

For this particular variant, it is important to ensure that appropriate quantities of the two (or more) components are provided so that minimal unreacted material is injected into the patient. It could be advantageous to package the two liquids in one container so that they are dispensed in equal amounts. The side-by-side syringe arrangement commonly used for epoxy adhesives is a good method. An alternative would be to deliver the two liquids through a volumetric pump (a pump whose volume delivery is controllably defined by the geometry), such as a gear pump or syringe pump, in contrast to a centrifugal pump.

Another embodiment contemplated by the invention employs cavitation to create microbubbles on demand in a liquid. More generally, cavitation involves creating a low pressure region locally in a liquid by means of mechanical forces, such as those resulting from rotation of a marine propeller. Because of the low pressure, some of the gas dissolved in the liquid comes out of solution, forming bubbles. Once formed, the bubbles are not immediately destroyed when the pressure returns to the steady state condition.

Figure 8A:
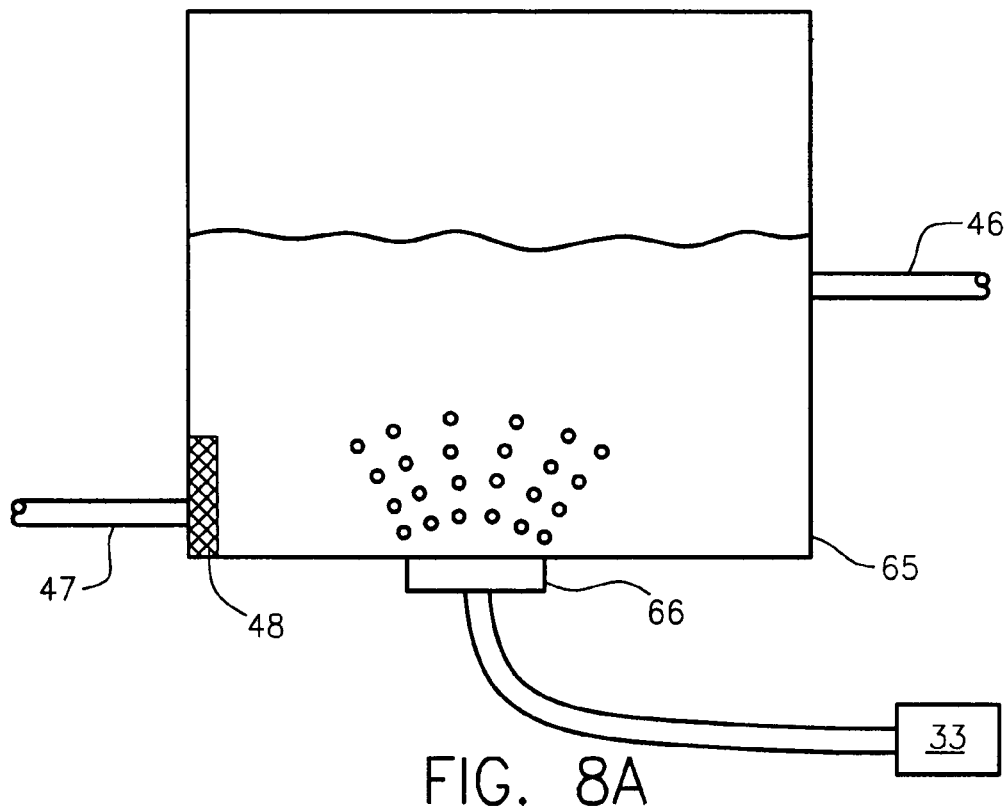
FIGS. 8A and 8B illustrate a sixth embodiment of the bubble generator of FIGS. 2A-2B.
Figure 8B:
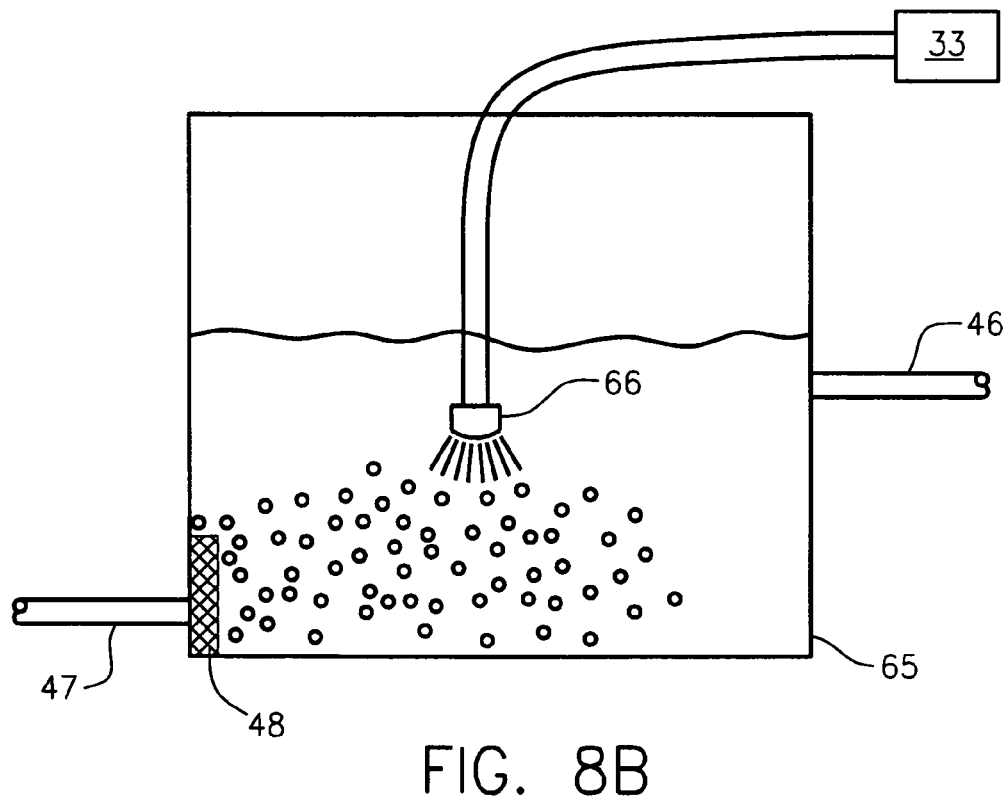

In the preferred manifestation of this embodiment as shown in FIGS. 8A and 8B, the microbubble generator includes an enclosure 65, a transmitter 66, the two fluid path conduits 46 and 47 and, optionally, filter 48. In response to a control signal from controller 33, the transmitter 66 would transmit ultrasonic energy to create the localized region of low pressure within the liquid wherein the microbubbles of gas would be formed. The resulting medium of microbubbles and the carrier liquid would then be directed through filter 48, and exit enclosure 65 through outlet conduit 47 from which it is to be conveyed to the patient via connector assembly 40, tubing 18 and catheter 22.

The transmitter 66 functions as a means for agitating the liquid so as to make the microbubble generator operate as described. Transmitter 66 can be situated within the liquid which ensures good energy transmission, as in FIG. 8B. Alternatively, as shown in FIG. 8A, the transmitter can be placed outside the enclosure, which allows for more easy manufacture and assembly of the fluid path and reusability of the transducer but requires good mechanical contact with the enclosure 65. Instead of transmitter 66, various other devices or arrangements of devices that cause cavitation within the liquid, to create the microbubbles, may be employed.

For example, the counter-rotation disks 50 and 51 of FIGS. 4A and 4B and the stirring elements 59 and 59' of FIGS. 5A and 5B could operate in this way if they were submerged within the liquid. A single disk could work, too. As with the other microbubble embodiments, such an agitating means will generally require a motor for activation, seals and other mechanical components.

The preferred manifestation uses an ultrasound beam to create specific spots with a low enough pressure where cavitation can occur. This is sometimes called sonication. Use of nucleation particles or molecules in the liquid will facilitate the creation of microbubbles in the bulk of a liquid. Alternatively, a surface can be used as the nucleation site. A cylindrical surface similar to that illustrated in FIG. 6, or a flat surface such as one of the sides of the nozzle 62 shown in FIG. 7, may serve as a nucleation site. The flow of the fluid from inlet 46 to outlet 47 or the flow created by the ultrasonic energy are two exemplary ways to sweep the bubbles off the nucleation surfaces.

Creating microbubbles by cavitation and from a supersaturated gas are related phenomena. With a supersaturated gas, the gas wants to come out of solution at the normal pressure that exists. With cavitation, the gas will stay in solution at the normal pressure, but if the pressure is reduced by some means, then gas will come out of solution from the liquid and a bubble will be formed. The various embodiments described in relation to one implementation can be adapted to operate with the other.

Figure 9:
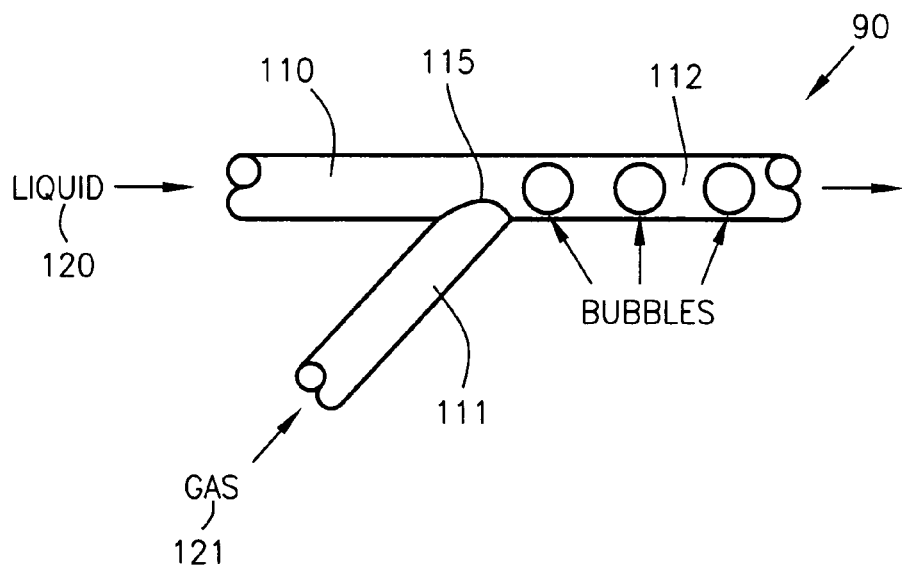
FIG. 9 illustrates a seventh embodiment of the bubble generator of FIGS. 2A-2B.

The invention also contemplates a family of microbubble generators that employ a gas-liquid interface structure through which to create the microbubbles on demand. FIG. 9 illustrates one such structure in which gas is injected into a liquid flow path in such a way that consistent microbubbles are created. Specifically, the microbubble generator includes a gas-liquid interface assembly 90 or, preferably, an array of such interface assemblies. Each such interface assembly 90 includes a liquid flow path 110 and a gas flow path 111. In the system of FIG. 2B, for example, the liquid flow path 110 would receive liquid 120 from primary container 30 via pump 31, and the gas flow path 111 would receive the gas 121 from secondary container 30" via pump 31". In operation, the liquid flow path 110 channels the pressurized liquid over the gas flow path 111 to entrain the gas 121 emanating therefrom as microbubbles in the liquid, with the resulting medium flowing out of fluid conduit 112 from which it is to be eventually conveyed to the patient via connector assembly 40, tubing 18 and catheter 22.

The liquid flow path has a diameter preferably on the order of 3 to 10 um. It could be formed in silicon by etching an appropriately sized groove therein. Alternatively, the flow path could be manufactured using a process similar to that used to create audio compact discs. This would take advantage of the significant improvements occurring in the MEM (Micro-Electro-Mechanical Systems) field of technology. The whole structure/array could then be very small, on the order of millimeters or less in size. To create $10^6$ microbubbles per second with a diameter of 10 um, a velocity of 3.3 m/sec for the liquid 120 and a velocity of 3.3 n/sec for the gas 121 could be used. This will work with any gas, and is not limited to carbon dioxide. Microbubbles of consistent size will be produced by this arrangement. The diameter of liquid path conduit 110 may be varying and/or different from that of gas path conduit 111, and both of them may be different from that of fluid conduit 112 into which the mixture flows. To produce microbubbles of the desired size, it is important that liquid 120 flows over the gas meniscus 115 at a velocity sufficient to sweep an appropriate amount of gas into the liquid to form each microbubble. The size of the microbubbles is thus a function of the volumetric flow rate of liquid 120; the volumetric rate at which gas 121 is injected; the diameter of fluid paths 110, 111 and 112; the angle of intersection between fluid paths 110, 111 and 112; and the properties of liquid 120 and gas 121 (e.g., viscosity and temperature).

The uniformity in the size of the microbubbles can be improved by providing a regular oscillation in either the liquid or the gas flow paths. This oscillation could be introduced by coupling an ultrasonic transducer to either flow path. It would provide an oscillatory motion in addition to the steady flow that drives the microbubbles out through fluid conduit 112. In the scenario described above, where $10^6$ microbubbles are to be created each second, the preferred frequency would be 1 MHz. This regular behavior would replace the chaotic pseudo-periodicity of a vortex shedding phenomenon or a random build up of pressure and breakthrough of one fluid into the other.

Figure 10:
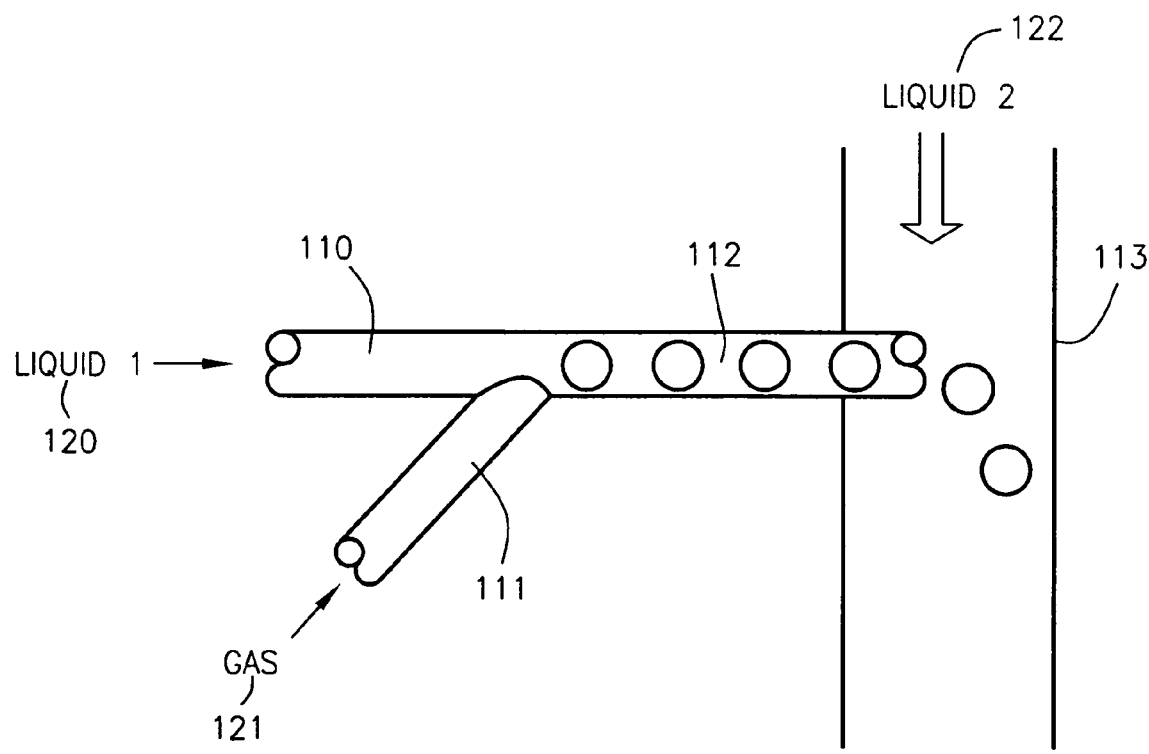
FIG. 10 illustrates an eighth embodiment of the bubble generator of FIGS. 2A-2B.

FIG. 10 illustrates an enhancement of the gas-liquid interface structure described above. Specifically, it shows fluid conduit 112 merged into a second liquid flow path 113 in which a second liquid 122 is flowing. In the system of FIG. 2B, for example, second liquid flow path 113 would receive the second liquid 122 from yet another container via yet another pump. The stream of microbubble-entrained liquid carried by the fluid conduit 112 would thus be injected into the second liquid 122, with the combined liquid stream in the second liquid flow path 113 then being carried eventually to the patient via connector assembly 40, tubing 18 and catheter 22 during the imaging procedure.

In the embodiments represented by FIGS. 9 and 10, the first liquid 120 is assumed to include a surfactant to stabilize the microbubbles. The first liquid 120 could be the same as the second liquid 122, or it could be that the first liquid 120 is selected with different properties to promote the stability of the microbubbles. The first liquid 120 therefore need not have the same composition as the second liquid 122. In either case, as roughly depicted in FIGS. 9 and 10, the amount of liquid between the microbubbles could be significantly more or even less than what is indicated.

In some diagnostic situations, it is desirable to include molecules that help target the microbubbles to specific physiological conditions such as plaque in the arteries, blood clots, inflammation, cancer, or heart muscle tissue that is oxygen deficient or damaged. Chemicals to accomplish this can be incorporated into either liquid 120 or liquid 122.

Because of the small size of the gas-liquid interface assembly 90 shown in FIGS. 9 and 10, it should be possible to have an array of such assemblies in parallel, each of which creating microbubbles that are injected into the second liquid 122. For example, an array consisting of ten, one hundred, or more such assemblies could be employed in the system shown in FIG. 2A and its variant shown in FIG. 2B.

Figure 11A:
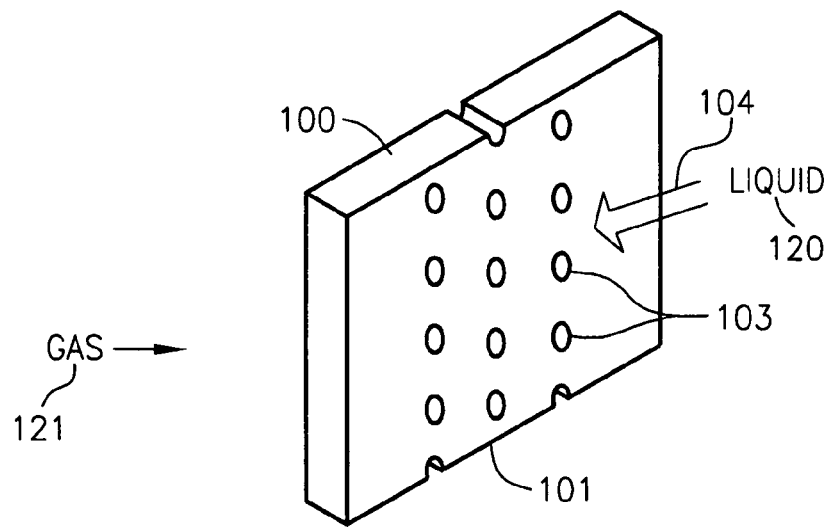
FIG. 11A illustrates a ninth embodiment of the bubble generator of FIGS. 2A-2B.
Figure 11B:
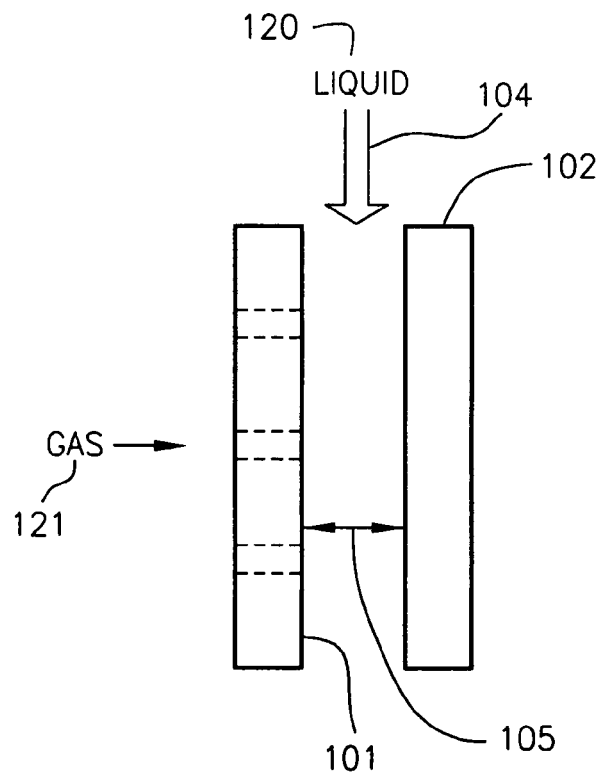
FIG. 11B illustrates a variation of the bubble generator shown in FIG. 11A.

Although forcing liquid through a small tube is a conceptually straightforward process, it has the disadvantage of requiring significant pressures. Consequently, an improvement upon the microbubble generators of FIGS. 9 and 10 would have the liquid flowing as a sheet over a plate containing an array of gas inlets. More specifically, as shown in FIGS. 11A and 11B, such a microbubble generator includes a gas introduction plate 100 having a plurality of gas inlets 103 over the surface of which is directed a liquid flow path 104. In the system of FIG. 2B, for example, the gas inlets 103 would receive the gas 121 from secondary container 30" via pump 31", with the liquid flow path 104 receiving the liquid 120 from the primary container 30 via pump 31. In operation, the liquid flow path 104 directs the liquid 120 as a sheet over the gas inlets 103 to entrain the gas 121 emanating therefrom as microbubbles in the liquid, with the resulting medium eventually conveyed to the patient via connector assembly 40, tubing 18 and catheter 22.

Compared to the embodiments shown in FIGS. 9 and 10, this gas-liquid interface not only significantly reduces resistance to the flow of liquid 120 but also allows multiple microbubbles to be created simultaneously. The gas introduction plate 100 is preferably micro-machined silicon, although various glasses or plastics could also be used. One benefit of plastic is that it is usually hydrophobic, so there would be little tendency for the liquid 120 to seep into the gas inlets 103. If a hydrophobic material is used for the introduction plate 100, then the surface 101 that contacts liquid 120 needs to be made sufficiently hydrophilic. Depending upon the plastic, a hydrophilic layer can be deposited on surface 101 by corona treatment or ultraviolet light. Such a hydrophilic layer can also be set down by plating, sputtering, or otherwise depositing a material on surface 101, or by other surface modification technologies known in the art.

FIG. 11B illustrates a variation on the gas-liquid interface structure described above in which a secondary plate 102 is disposed a predetermined distance 105 apart from gas introduction plate 100. In this variation, the liquid 120 is channeled between the two plates 100 and 102. Consequently, the predetermined distance 105 can be selected so as to yield microbubbles of the desired size. The secondary plate 102 may take the form of a solid plate. Alternatively, it could be manifested as a plate having a plurality of gas inlets by which more gas can be entrained in the liquid flowing through the flow path 104. The distance between the two plates 100 and 102 does not need to be the same as the desired microbubble diameter. It may be beneficial to have it several times the microbubble diameter because then, as they are created, the microbubbles move out into the main flow, so multiple rows of gas inlets can inject gas into the liquid 120. It is important, however, that plates 100 and 102 be close enough that the velocity of the liquid 120 at the surface of the plate(s) be sufficient to dislodge the microbubbles when they get to the desired size. Again, this depends upon gas and liquid flow rates and surface velocities, liquid viscosity, temperature, and the precise geometry involved. The gas inlets 103 are preferably 1 to 3 μm in diameter. This facilitates the separation of the microbubbles from the plate(s) when the microbubbles reach a diameter of 3 to 10 um.

In addition, as mentioned above, it can be beneficial to impose an oscillatory motion on the steady state flow of either the liquid 120 or the gas 121. This helps make the separation of the gas stream into discrete microbubbles more consistent and controllable.

Figure 12:
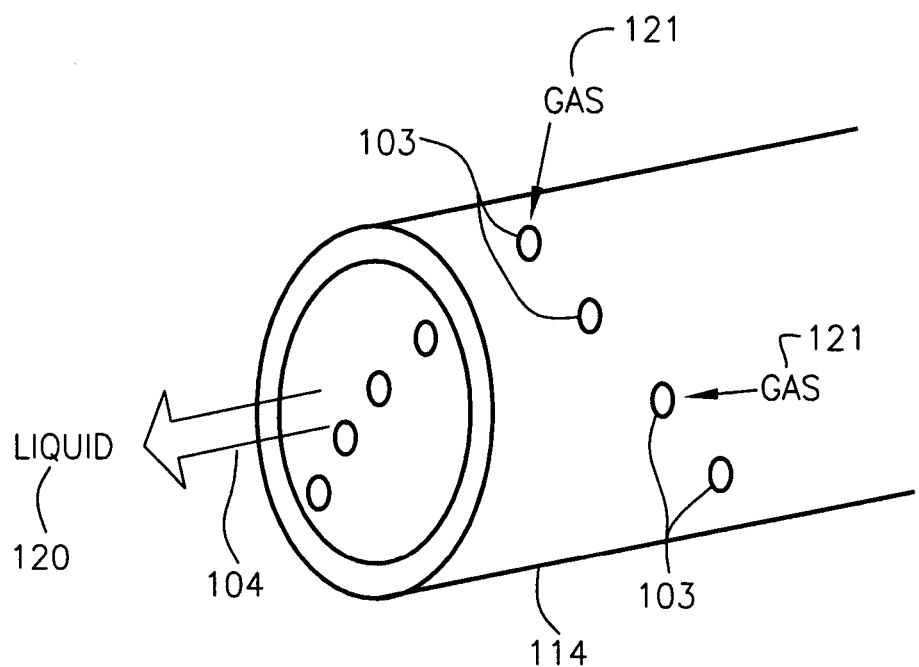
FIG. 12 illustrates a tenth embodiment of the bubble generator of FIGS. 2A-2B.

FIG. 12 shows another variation on the gas-liquid interface structure of FIG. 11A. In this variation, the gas introduction plate can be thought of as having been rolled up into a cylinder or tube. The tube 114 thus features a plurality of gas inlets 103. If incorporated into the system of FIG. 2B, the gas inlets 103 of tube 114 would receive the gas 121 from secondary container 30" via pump 31", with the liquid flow path 104 in the tube receiving the liquid 120 from the primary container 30 via pump 31. In operation, the liquid flow path 104 directs the liquid 120 over the gas inlets 103 to entrain the gas 121 emanating therefrom as microbubbles in the liquid. The resulting medium would be then conveyed to the patient via connector assembly 40, tubing 18 and catheter 22.

Figure 13A:
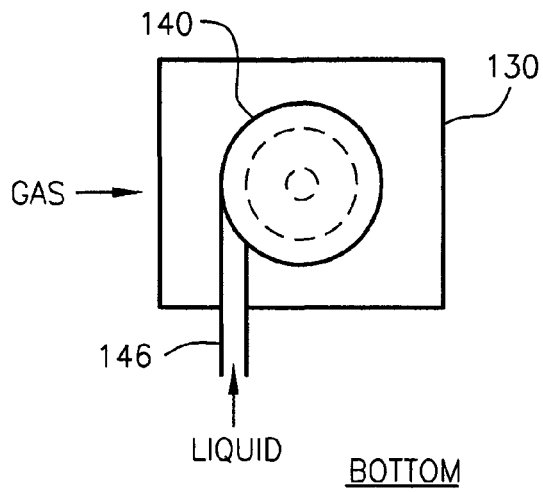
FIGS. 13A-13C illustrate bottom, top and sectional views of an eleventh embodiment of the bubble generator shown in FIGS. 2A-2B.
Figure 13B:
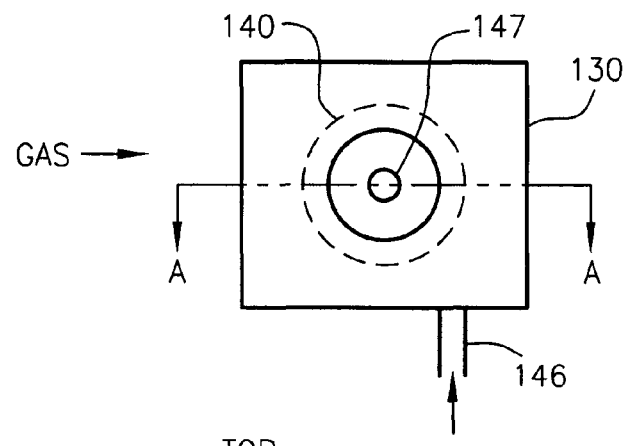
Figure 13C:
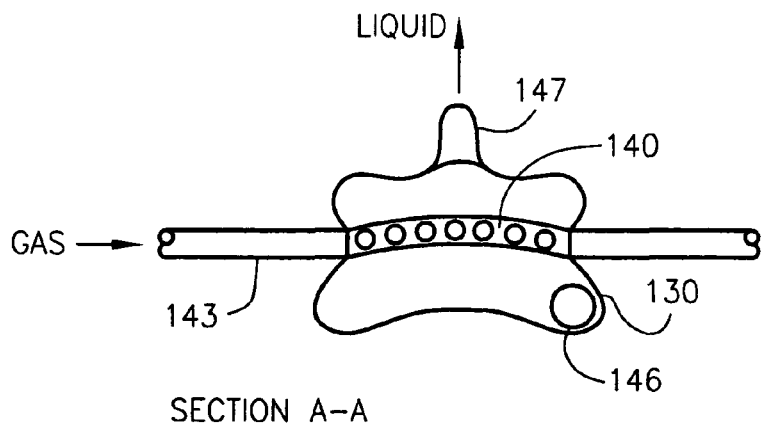

FIGS. 13A-13C illustrate another embodiment of microbubble generator, one that couples centrifugal force with the flow of liquid over a surface having one or more gas inlets. This embodiment of microbubble generator includes a chamber 130 and a liquid flow path 140 defined therein. The liquid flow path 140 has a generally helicoidal-shaped portion, with an inlet conduit 146 at its bottom end and an outlet conduit 147 at its top end. The gas inlet(s) 143 are defined in a wall of the liquid flow path 140.

In the system of FIG. 2B, for example, the inlet conduit 146 would receive the liquid from primary container 30 via pump 31, and the gas inlet(s) 143 would receive the gas from secondary container 30" via pump 31". In operation, the liquid would flow into inlet conduit 146 then tangentially into the liquid flow path 140 in the bottom half of chamber 130. Due to the helical path defined by liquid flow path 140, the velocity of the liquid will have both tangential and radial components. The liquid will therefore spin and rise upward as it flows toward the outlet conduit 147. During the course of its flow, the liquid is channeled over the gas inlet(s) 143 so that the gas emanating therefrom is entrained as microbubbles in the liquid. Because of the conservation of angular momentum, the liquid spins faster as it passes the gas inlet(s). In addition to the effect of the radial component of the velocity (perpendicular to the surface of the gas inlet(s)), the spinning of the liquid amplifies the buoyancy of the gas microbubbles, creating an additional force that pulls the microbubbles off the gas inlet(s) and toward the center. The resulting contrast medium exits the chamber 130 through outlet conduit 147 from which it is to be conveyed to the patient via connector assembly 40, tubing 18 and catheter 22. A filter may be used to further ensure that only microbubbles with the desired size distribution are provided to the patient.

It is also possible to use centrifugal force in the microbubble generator embodiment illustrated in FIG. 12. There could be a spiral vane upstream of the tube section 114 shown in FIG. 12 that imparts a twisting or spinning motion to the liquid.

For the class of microbubble generators that introduce gas into a liquid, there is a remote possibility that the flow of liquid could be blocked, in which case the flow of gas could continue. In a worst case scenario, the gas could be injected into the patient. There are several ways, however, to prevent this from occurring. First, the supply of gas could be shutoff when the flow of liquid drops below a specified level. This task could be performed by the fluid monitor 35 shown in FIGS. 2A and 2B. It could include or take the form of a simple pressure sensor placed at the output of microbubble generator 32, with the exact pressure level at which the system will be disabled being dependent upon the programmed flow rate. Second, the fluid monitor 35 could include or take the form of a fluid assurance detector that stops the flow of gas when it detects that the majority of the fluid in any given conduit is a gas rather than a liquid. Available fluid assurance devices are based upon ultrasonic or optical energy transmission. Third, the flow of the liquid itself could be used to pull the gas into the liquid. A common device that uses this principle is the water power aspirator used in high school and college chemistry labs. Flowing water entrains air and creates suction for filtering a reaction product. In this instance, however, a somewhat more sophisticated mechanism is needed because the liquid is at a net positive pressure to allow it to pass through a catheter and into the patient. A gas pressure regulator could be used to maintain the pressure of the gas slightly below the pressure of the liquid at the inlet of the microbubble generator. As the flow of liquid accelerates through the microbubble generator, it will then create a negative pressure that pulls the gas into the liquid. This scheme will also work with a pulsatile flow superimposed on the steady state flow of the gas or liquid.

FIG. 14 illustrates an embodiment of microbubble generator that uses two liquids and a gas to produce the microbubbles. Liquid 1 is water-based, or hydrophilic, whereas liquid 2 is a hydrophobic liquid. The microbubble generator includes two members 160 and 161. Member 160 has outer and inner surfaces 162 and 164 between which are defined one or more inlet holes 133, which are preferably only a few microns in diameter. The surface 164 of member 160 is hydrophilic so that liquid 2, the hydrophobic liquid, does not wet it. Surface 162 is hydrophobic, as are the surfaces 162a of inlet holes 133. Member 161 has inner and outer surfaces 163 and 165, hydrophobic and hydrophilic, respectively, between which are defined one or more outlet holes 153. The surfaces 163a of outlet holes 153 are also hydrophobic. Members 160 and 161 could be made of a plastic such as Teflon or polypropylene that are corona, UV or otherwise treated to form the hydrophilic surfaces. Alternatively, they could be metal plates with a plastic coating applied to make them hydrophobic in the proper areas. As in all the embodiments discussed, liquid 1 and liquid 2 may optionally both be hydrophilic or hydrophobic, or be the same liquid, and the surfaces can then be selected appropriately. The system of FIG. 2A, for example, can accommodate this microbubble generator if one such liquid is used.

In the system of FIG. 2B, two different liquids can be used. Liquid 1 could be provided from primary container 30 via pump 31, liquid 2 from secondary container 30" via pump 31", and the gas from yet another container via yet another pump. In operation, the gas is infused into the gap 166 between the inner sides 164 and 163 of members 160 and 161. From the outer side 162 of member 160, a droplet of liquid 2 would then be directed through the inlet and outlet holes 133 and 153 and thus through the intervening layer of gas in gap 166. Upon impact of the droplet on the surface of liquid 1, a microbubble is created from those constituent elements. If liquid 1 has a surfactant as part of its mixture, then liquid 2 and the gas will form the microbubble with the droplet of liquid 2 either inside the microbubble or incorporated into its shell. If the holes 133 and 153 are of similar size, then as a droplet of liquid 2 moves from hole 133 to hole 153, it traps the gas that is in the hole 153 and drives the resulting microbubble out into liquid 1. Members 160 and 161 will ideally have an array of such passageways or holes 133 and 153 so that a great quantity of microbubbles can be created simultaneously. The droplets of liquid 2 for such an array can be generated using any of the technologies commonly employed in today's Inkjet printers, with piezoelectric and thermal "boiling" being the two most commonly used techniques. The resulting microbubble contrast medium generated by the array would be conveyed to the patient via connector assembly 40, tubing 18 and catheter 22.

This embodiment of microbubble generator is particularly well suited to create microbubbles that can be tagged with materials to cause selective binding within the body. It also provides a very good way of creating microbubbles that contain materials for ultrasound-controlled release into the tissue to be treated.

FIG. 15 shows another microbubble generator that uses two liquids and a gas. Liquid 1 could be water-based and liquid 2 hydrophobic, or vice versa. Alternatively, liquid 1 and liquid 2 could both be water-based or hydrophobic. In one possible configuration, the microbubble generator includes a housing 179 and two outer surfaces 181 and 184 on opposite sides thereof. The housing 179 includes a cell chamber 189 or, preferably, a plurality of such cell chambers. Each cell chamber 189 defines two liquid flow paths 191 and 194 and, preferably, a gas flow path 193, all three of which intersect each other. The inner surface(s) 182 and 183 of gas flow path 193 are chosen or appropriately treated to prevent the entry of either liquid into the gas flow path 193. Alternatively, the geometry of the flow paths can be designed to prevent seepage of liquid into gas flow path 193.

In the system of FIG. 2B, for example, liquid 2 could be provided from primary container 30 via pump 31, liquid 1 from secondary container 30" via pump 31", and the gas from yet another container via yet another pump. Liquid 2 would be in contact with surface 181 and liquid flow path 191, liquid 1 with surface 184 and liquid flow path 194, and the gas routed to gas flow path 193. In a preferred manifestation, liquid 2 could be a foaming agent, surfactant or encapsulating chemical with which to form the shell of the microbubble, with liquid 1 being the carrier of the microbubbles.

In operation, the gas is injected into gas flow path 193 with the goal of forming a microbubble at the intersection of flow paths 191 and 194 where liquids 1 and 2 meet. The liquid 2 in liquid flow path 191 is then similarly pressurized, which enables creation of the microbubble with liquid 2 forming its shell. As a result of the pulsed pressurization of liquid 2, the resulting microbubble will be thrust into and pass through flow path 194 and be ejected into the flow of liquid 1 outside surface 184. In a housing 179 having an array of cell chambers 189, a great quantity of microbubbles can be created simultaneously. Liquid 1 and the microbubbles it carries would be then conveyed to the patient via the connector assembly 40, tubing 18 and catheter 22, as shown in FIG. 2B.

The arrangement of FIG. 15 can be used without the gas and its corresponding gas flow path 193. This can be accomplished if liquid 2 is supersaturated with a gas and the injection of liquid 2 into liquid 1 releases some of the gas to form the requisite microbubble. Alternatively, liquid 2 could be chosen so that it reacts with liquid 1, or a reaction is catalyzed with liquid 1, such that gas is evolved and a microbubble is formed.

FIG. 16 illustrates another embodiment of microbubble generator, one in which there is no flow of gas. The two liquids 1 and 2 it uses are preferably dissimilar, with liquid 2 being hydrophobic and liquid 1 hydrophilic or water based. Liquid 2 is actually mixture of two fluids, with one fluid having a lower boiling point than the other fluid. In one possible mixture, liquid 2 can have one fluid whose boiling point ranges generally between 37° C. and 20° C. and another fluid whose boiling point is higher.

The microbubble generator itself includes a plate 170 having a first surface 171 and a second surface 173 with an inlet hole 172 extending therebetween. It also features at least one heater 175 in communication with a wall of the inlet hole 172, which together can be referred to as an nozzle or interface assembly 174. The first surface 171 and the wall of inlet hole 172 are hydrophobic and in contact with liquid 2 on one side of plate 170. The second surface 173 is hydrophilic and in contact with liquid 1.

The microbubble generator operates by exploiting a mechanism similar to that used in thermal Inkjet printers. More specifically, upon application of a rapid pulse of energy to heater 175, the heater boils the liquid 2 that touches it. The constituent fluids in the affected liquid 2 both vaporize and form a bubble, and this bubble is carried out into liquid 1 that is flowing outside second surface 173. The pressure to drive the flow of liquid 2 could be provided by capillary action or some other pressurizing or pumping device. As the gas in the bubble cools, the vaporized fluid with the lower boiling point will remain a gas, but the other vaporized fluid (i.e., the one that has the higher boiling point) will condense back into a liquid and incorporate itself into the shell of the resulting microbubble. The technology of thermal Inkjet printers allows arrays of tens or hundreds of such nozzle type microbubble generators to be created.

An alternative use of the structure of FIG. 16 could employ a liquid 2 that already contains many microbubbles, but is not suitable for immediate injection into a patient. This could be due to the need to stabilize the microbubbles, or simply because liquid 2 is too viscous to deliver effectively. An arrangement such as that shown in FIG. 16, coupled with other technology previously disclosed herein, would allow metering of the insertion of liquid 2 with its microbubbles into liquid 1 for subsequent delivery to the patient. This alternative would have the advantage of using liquid 2 (which would be very concentrated and expensive) with liquid 1 (which would be inexpensive), resulting in a significant cost savings over current practice.

The microbubble generators of the invention can also be used with bodily fluids. Such fluids can be withdrawn from the patient, optionally mixed with additional fluid(s), manipulated to create the microbubbles therein, and then returned to the patient. The microbubble generators make this relatively easy to do because the microbubbles can easily be created in close proximity to the patient. Blood would be the most typical fluid to use, as most procedures put microbubbles in the blood stream for image contrast or drug delivery. Blood contains a complex mixture of water and many other molecules that can act as surfactants to stabilize the microbubbles. The blood could be withdrawn and injected into a single vein through a dual lumen IV catheter so that minimal complication would be added to any such procedure. For the low flow rates needed, this is sufficient.

Withdrawing and re-injecting fluids is especially useful for imaging fluid structures that do not involve blood vessels, such as regions of the body containing cerebrospinal fluid. Because such regions are relatively closed systems, injecting any extra fluid could cause slight to serious problems independent of the chemical properties of the liquid injected.

With the flexibility and features of the invention described herein, many innovations and improvements can be made to the practice of medicine. One relates to U.S. Pat. No. 6,397, 098 cited above, which teaches the innovation of feeding back information from the ultrasound scanner 26 to the injection controller 33. In that patent, the concept of changing the rate of flow or dilution (concentration) of the microbubbles was disclosed. The present invention is an alternative to, or expansion of, that disclosed in U.S. Pat. No. 6,397,098 because the microbubble generators herein can be controlled to increase, reduce or maintain the number of microbubbles flowing into the patient per unit time.

The microbubble generation rate is a function of many factors depending upon the specific implementation. The rate at which a generator can produce microbubbles can be scaled to achieve the rate necessary for a wide variety of applications. For example, multiple disks could be used in relation to the embodiment shown FIGS. 4A and 4B. Multiple fluid paths could be employed to increase the microbubble generation rate of the generator embodiment illustrated in FIG. 9. Multiple microbubble generators and operating many or all of them in parallel is an approach. The flow rates of liquids and/or gases also will influence the rate at which the microbubbles are generated. In addition, the frequency of any periodic excitation affects the microbubble generation rate.

To achieve microbubble generation rates less than the maximum, the microbubble generators of the present invention can be controlled by a number of strategies. The simplest involves something similar to pulse width modulation or time domain modulation. The generator is either fully on, producing N microbubbles per second, or off. The ratio of on-time to off-time, or duty cycle, can be used to change the rate of microbubble generation from 0 to N microbubbles per second. Some of the generators disclosed herein implicate other variables that could be used to control the microbubble size or creation rate. For those embodiments in which a gas flows under pressure into the microbubble generator, changing the rate at which the gas flows will change the number of microbubbles created per unit time, especially in those instances where the microbubbles are swept from the surfaces when they reach a specific size. Other microbubble generators (e.g., FIGS. 8A and 8B) use ultrasonic pressure waves to control the ejection of gas into the liquid. Varying the frequency or amplitude of this pressure wave will change or modulate the size or number of microbubbles created per unit time. For those generator embodiments that employ mechanical agitation or motion (e.g., FIGS. 3, 4A-4B and 5A-5B), changing the amplitude, frequency or speed of the mechanical excitation will affect the microbubble generation rate. For those embodiments having an array of microbubble generating structures (e.g., FIGS. 9, 10, 15 and 16), the number of generating structures active at any one time could be varied with time.

Each of these embodiments offers an indication of how the controller 33 of systems 1 and 2, as shown in FIGS. 2A and 2B, can affect the rate at which the microbubble generator 32 creates microbubbles. For example, the flow through the microbubble generator 32 can be mixed or diluted with another liquid stream of the same or a different liquid if a specific concentration of bubbles (#/ml) is needed in addition to a specific bubble rate (#/sec) at a specific total liquid flow rate (ml/sec) because the flow rate through the bubble generator may be specific to the size of the bubbles to be generated. Of course, once two of these variables are selected or specified, the third is thereby determined. FIG. 10 in one mode of operation explicitly shows bubble concentration dilution by the addition of another liquid. It can be used with all other bubble generators, and can be done anywhere downstream of the bubble generator.

Apart from microbubble generation, the techniques of U.S. Pat. No. 6,317,623 can be used to monitor the size and/or concentration of microbubbles, and to selectively destroy microbubbles to achieve the necessary concentration and size distribution.

The microbubble generators disclosed herein also have application beyond immediate injection into the patient. They could be used to prepare microbubbles for subsequent injection, e.g., later in the day, or even days later. Exemplary methods of storage include refrigerating or freezing the liquid containing the microbubbles. Alternatively, more sophisticated means could be used, such as those used in the pharmaceutical industry. The benefits of the microbubble generators disclosed above, such as tight size distribution and precise rate and thus concentration control, could then be made available at locations where the microbubble generators themselves might not be available.

With many of the microbubble generator embodiments described above, the systems 1 and 2 of FIGS. 2A and 2B can control the microbubble size distribution much more tightly than is possible with current methods. The best methods for creating a tight distribution are those with geometry controlled microbubble generation, usually involving pits or holes in a solid surface and fluid flow over that surface that dislodges the microbubbles when they reach a specific size. With a tight size distribution, it is possible to tune more selectively the ultrasound imager 26 to the microbubbles that are present and reject other sources of noise. Alternatively, the ultrasound scanner 26 can be swept through a range of frequencies and, based upon the peak in the amplitude response vs. frequency, a measure of the microbubble diameter can be determined. The narrow diameter distributions that can be created with the invention disclosed herein more effectively allow the monitoring of changes in microbubble diameter within the body.

Monitoring microbubble diameter could allow monitoring of blood pressure inside vessels. (U.S. Pat. No. 6,302,845 to Shi et al., incorporated herein by reference, discloses a method of measuring pressure with the blood vessels.) Blood pressure is commonly measured in mm of mercury, where 760 mmHg is 1 atmosphere or 101 KPa. Blood pressure can vary from 100 mmHg to 200 mmHg peak and 50 mmHg to 100+mmHg. A change of 76 mmHg would result in a 10% bubble volume change and thus a 3.2% change in bubble diameter. Monitoring the change in diameter would therefore give an indication of blood pressure. This would be especially useful when trying to determine the hemodynamic significance of blood vessel blockages. If the pressure downstream from the vessel restriction is too low, then the pressure drop is high and the blockage needs to be treated. If it is not much different than before the restriction, it can be watched and intervention postponed. Measuring blood pressure downstream of a restriction normally requires placing a catheter in the vessel and moving it past the blockage. That current practice is relatively risky because the catheter can knock material from the blockage and cause an embolism downstream. In addition, putting a catheter into the arterial system causes significantly more trauma to the patient than a simple intravenous catheter used to administer microbubbles to the body. Thus, the present invention enables a new method of non-invasively or minimally-invasively measuring blood pressure in specific blood vessels. In this application, the preferred microbubbles will be composed of a gas that does not quickly diffuse out of the bubble and have a shell that does not let gasses quickly diffuse in from the blood.

Another way to exploit the benefits of tight size distribution so as to enable new medical procedures is to select the wall material so that oxygen and/or carbon dioxide gas can quickly diffuse into or out of the microbubbles. When this happens, the diameter(s) of the microbubbles will change. The amount of gas that will diffuse is determined by the oxygen or carbon dioxide in the blood. In this way, blood gas concentrations may be measured non-invasively or minimally-invasively. By selecting the initial gas and the wall material, this property can be optimized. One difficulty with this is that blood pressure will also change microbubble diameter, as discussed previously. One way to overcome this difficulty is to compare bubble diameter changes in nearby but normal tissue with those in the tissue under study. An alternative is to use two different types of microbubbles, each of which having different responses to blood gasses.

Before the present invention, ultrasound contrast techniques lacked the ability to produce two discretely separate bubble populations. By using two microbubble generators, either in series or in parallel, two different bubble populations can be created. They could differ in size, for instance 3 um and 10 um. They could have different gases, or different shell or surfactant properties. One could contain a specific drug and the other not.

By having two discrete bubble populations, it is also possible to separate the effect of pressure from the effects of gas diffusion. Larger microbubbles respond more slowly to gas diffusion because they have a smaller surface area to volume ratio. Thus, during the time that gas diffusion has not reached steady state, larger microbubbles would respond less to blood gasses than smaller microbubbles. The response of the microbubbles to blood pressure, however, is purely determined by geometry.

As noted above, the surface properties of the microbubbles can be selected to allow the targeting of various physiological states or conditions. There could be a benefit to creating two or more different populations of microbubbles with different chemical properties. Alternatively, one population can be for diagnosis and the second population can consist of microbubbles containing therapeutic chemicals that are released upon the destruction of the microbubbles. More than two populations of microbubbles can be created, of course, and would have advantages in various clinical situations.

Furthermore, having precise control of the gas used to form the microbubbles also provides a number of options. The gas could be pure oxygen. This could be used intra-arterially or intravenously to assist a patient with an acute need. Alternatively, it could also be part of a diagnostic procedure.

The present invention could also be used to create a medium with a high density of bubbles and thus large amounts of gas (e.g., $CO_2$) to create a carbon dioxide foam which will have a very low density compared to water. The foam could be injected into a blood vessel as an X-ray contrast. The use of carbon dioxide gas as an X-ray contrast has been known for many years. The main problem has been ensuring that the gas delivery line is purged of air and filled with $CO_2$. The other problem is the tendency for "bubbles of blood" to remain on the vessel wall after the vessel is filled with $CO_2$. U.S. Pat. No. 6,231,513, incorporated herein by reference, describes using a catheter to create microbubbles of carbon dioxide in a vessel. Creating a foam with carbon dioxide outside of the body for subsequent injection has several benefits. One is that the presence of fluid and the absence of air in the fluid lines can be visually monitored, whereas there is no way to determine whether a fluid line is filled with air or $CO_2$. The second is that the foam will better displace blood, preventing a droplet or "negative bubble" of blood from simulating a plaque on the inside of a vessel wall.

The preferred embodiments above constitute examples of particular orderings of the fluid reservoirs, pumps, and other fluid path conduits. Someone skilled in the art could reorder or rearrange these components and successfully create microbubbles as needed. In addition, several of the bubble generators presented herein employ flow paths, tubes, pipes, fluid conduits and other structural features. These structural features can be implemented in various ways. For example, a pair of flat plates—if suitably modified—can, when coupled together, be used to define these structural features. Similarly, some of the bubble generators employ plates or other members. Instead of being implemented as flat structures, such plates and members can be manifested in the alternative as curved surfaces, suitably modified for the specific application for which they are intended.

The presently preferred and alternative embodiments for carrying out the invention have been set forth in detail according to the Patent Act. Persons of ordinary skill in the art to which this invention pertains may nevertheless recognize alternative ways of practicing the invention without departing from the spirit of the following claims. Consequently, all changes and variations which fall within the literal meaning, and range of equivalency, of the claims are to be embraced within their scope. Persons of such skill will also recognize that the scope of the invention is indicated by the following claims rather than by any particular example or embodiment discussed in the foregoing description.

Accordingly, to promote the progress of science and useful arts, we secure for ourselves by Letters Patent exclusive rights to all subject matter embraced by the following claims for the time prescribed by the Patent Act.

What is claimed is:

1. A method of preparing a medium with bubbles formed therein and contemporaneous injection into a patient in connection with a medical procedure, the method including the steps of:
    (a) providing a source of a liquid and a source of a gas;
    (b) providing a bubble generator wherein the bubbles are created within the liquid to form the medium, said bubble generator having at least one inlet for receiving the liquid and the gas from said sources thereof and an outlet from which the medium is output;
    (c) providing a pressurizing device for pressuring the liquid for conveyance into said bubble generator and thereby for conveying therefrom the medium formed therein; and
    (d) providing a controller for controlling at least said pressuring device and said bubble generator through which to control (I) a rate of flow of the liquid and a rate of flow of the gas into said bubble generator via said at least one inlet thereof, (II) at least one property of the medium and (III) a rate flow of the medium from said bubble generator via said outlet thereof; and
    (e) communicating from said bubble generator via said outlet thereof the medium immediately after formation thereof so as to inject the medium into the patient in connection with the medical procedure at a rate controlled by said controller.

2. The method of claim 1 wherein the step of injecting the medium immediately after formation thereof into the patient comprises using a catheter that is inserted into a suitable vessel of the patient and an associated tubing set through which the medium in communicated from said outlet of said bubble generator via said catheter into the patient.

3. The method of claim 1 wherein said pressurizing device includes at least one of a gear pump, a peristaltic pump, a syringe pump and a centrifugal pump.

4. The method of claim 1 wherein the medical procedure is one of an imaging procedure carried out using an imaging unit and a therapeutic procedure.

5. The method of claim 1 wherein said controller enables control of the at least one property of the medium using at least feedback from an imaging unit used during the medical procedure.

6. The method of claim 1, 4, or 5 wherein the properties of the medium include composition of the medium, composition of the bubbles in the medium, concentration of the bubbles in the medium, size of the bubbles in the medium, rate of flow of the medium, volume of the medium administered, timing of the administration of the medium, sequencing of the administration of the medium, pressure of the medium, temperature of the medium, and viscosity of the medium.

7. The method of claim 1 further comprising using a fluid verification device disposed between said bubble generator and the patient, said fluid verification device for at least one of monitoring and changing at least one of the properties of the medium.

8. The method of claim 7 wherein said fluid verification device is capable of at least one of (i) detecting an unacceptably large amount of the gas and preventing administration thereof to the patient and (ii) destroying any of the bubbles having a diameter at least one of greater than, less than, within, and outside a predetermined range of sizes.

9. The method of claim 7 wherein said controller at least one of communicates with and controls operation of said fluid verification device.

10. The method of claim 7 wherein said controller controls operation of at least one of said pressurizing device and said bubble generator based at least in part on information from said fluid verification device.

11. The method of claim 1 wherein said bubble generator creates the bubbles by entraining the gas into the flow of the liquid to form the medium.

12. The method of claim 11 further comprising using a fluid verification device disposed between said bubble generator and the patient, said fluid verification device for preventing injection of the medium into the patient upon at least one of the rate of flow of the medium dropping below a specified level and detecting that the medium contains an unacceptably large amount of the gas.

13. The method of claim 1 wherein said bubble generator comprises:
    (a) an enclosure within which to agitate the liquid in presence of the gas; and
    (b) a means for disrupting an interface between the liquid and the gas, said disrupting means being responsive to a control signal from said controller by agitating said interface thereby creating the bubbles of the gas within the liquid.

14. The method of claim 1 wherein said bubble generator comprises:
    (a) an enclosure within which to agitate the liquid in presence of the gas;
    (b) a mechanism for agitating associated with said enclosure, said mechanism being responsive to a control signal from said controller by agitating an interface between the liquid and the gas thereby creating the bubbles of the gas within the liquid; and
    (c) a filter disposed proximate said outlet for removing from the medium any of the bubbles having a diameter greater than a predetermined size.

15. The method of claim 1 wherein said bubble generator comprises:
    (a) an enclosure within which to place the liquid in presence of the gas;
    (b) two disks disposed in said enclosure, said disks separated by a gap of a preset thickness and capable of being spun;
    (c) a mechanism for spinning said disks, said mechanism being responsive to a control signal from said controller by spinning said disks thereby compelling the liquid to flow into said gap resulting in creation of the bubbles of the gas within the liquid; and
    (d) a filter disposed proximate said outlet of said enclosure for removing from the medium any of the bubbles having a diameter greater than a predetermined size.

16. The method of claim 1 wherein said bubble generator comprises:
    (a) an enclosure within which to place the liquid in presence of the gas;
    (b) a stifling element disposed in said enclosure;
    (c) a mechanism for moving said stirring element, said mechanism being responsive to a control signal from said controller by moving said stirring element thereby causing the creation of the bubbles of the gas in the liquid; and
    (d) a filter disposed proximate said outlet of said enclosure for removing from the medium any of the bubbles having a diameter greater than a predetermined size.

17. The method of claim 16 wherein said stirring element comprises multiple small wires.

18. The method of claim 1 wherein the liquid is supersaturated with the gas under pressure and has nucleation materials therein, with said bubble generator comprising a nozzle such that as the liquid passes therethrough the pressure of the liquid decreases causing the bubbles of the gas to form on the nucleation materials and come out of and entrain with the liquid, thereby forming the medium.

19. The method of claim 18 wherein the nucleation materials comprise at least one of particles and chemicals.

20. The method of claim 1 wherein the liquid is supersaturated with the gas under pressure as the liquid enters said bubble generator, with said bubble generator comprising a nozzle having a plurality of nucleation sites formed therein such that as the liquid passes through said nozzle and contacts at least one of said nucleation sites the pressure of the liquid decreases causing the gas to come out of solution, forming the bubbles that entrain with the liquid thereby forming the medium.

21. The method of claim 20 wherein said nucleation sites take the form of pits formed in an inner wall of said nozzle.

22. The method of claim 20 wherein said nozzle is cylindrical in shape.

23. The method of claim 20 wherein said nozzle comprises plates attached together to form a pipe, with at least one of said plates bearing said nucleation sites.

24. The method of claim 1 wherein said bubble generator comprises:
    (a) an enclosure within which to place the liquid in which the gas is dissolved; and
    (b) a device, controlled by said controller, to apply energy to the liquid to create localized regions of gas supersaturation thereby enabling creation of the bubbles of the gas within the liquid to form the medium.

25. The method of claim 24 wherein said localized regions of gas supersaturation comprise regions of reduced pressure created by at least one of mechanical motion, an oscillatory pressure component, and an oscillatory flow component.

26. The method of claim 1 wherein said bubble generator comprises:
    (a) an enclosure within which to place the liquid in which a gas is dissolved; and
    (b) a transmitter for transmitting ultrasonic energy into the liquid to cause cavitation therein thereby enabling creation of the bubbles of the gas within the liquid to form the medium.

27. The method of claim 1 wherein said bubble generator comprises:
    (a) a liquid flow path for receiving via said at least one inlet the liquid from said pressurizing device; and
    (b) a gas flow path in communication via said at least one inlet with said source of the gas for directing the gas received therefrom to said liquid flow path;
    with said liquid and said gas flow paths constituting a gas-liquid interface assembly such that said liquid flow path channels the liquid received from said pressurizing device to an intersection with said gas flow path to entrain the gas emanating therefrom as the bubbles, thereby forming the medium for communication from said outlet.

28. The method of claim 27 wherein said controller operates said pressurizing device and said source of the gas to produce an oscillatory component to the flow within at least one of the gas flowing in said gas flow path and the liquid flowing in said liquid flow path.

29. The method of claim 27 wherein said bubble generator comprises an array of said gas-liquid interface assemblies.

30. The method of claim 27 wherein said bubble generator further comprises a fluid flow path for receiving a second liquid from said pressurizing device and for channeling the second liquid received therefrom into the liquid into which the gas has been entrained, thereby further forming the medium for communication from said outlet.

31. The method of claim 30 wherein said bubble generator comprises an array of said gas-liquid interfaces.

32. The method of claim 1 wherein said bubble generator comprises:
   (a) a gas introduction plate having a plurality of gas inlets in communication with said source of the gas via said at least one inlet; and
   (b) a liquid flow path for receiving via said at least one inlet the liquid from said pressurizing device and for channeling the liquid received therefrom over said gas introduction plate to entrain as the bubbles the gas emanating from said gas inlets, thereby forming the medium for communication from said outlet.

33. The method of claim 32 wherein said controller operates said pressurizing device and said source of the gas to produce an oscillatory component to the flow within at least one of the gas flowing in said gas inlets and the liquid flowing in said liquid flow path.

34. The method of claim 32 wherein said bubble generator further comprises a secondary plate disposed a predetermined distance apart from said gas introduction plate between which the liquid is channeled by said liquid flow path, said predetermined distance being selected to affect a size of the bubbles so entrained.

35. The method of claim 34 wherein said secondary plate has a plurality of gas inlets by which the gas is further so entrained by the liquid flowing in said liquid flow path.

36. The method of claim 1 wherein said bubble generator comprises:
   (a) a tube having a plurality of gas inlets defined in a wall thereof and one end for receiving the liquid from said pressurizing device, with said gas inlets adapted for communication via said at least one inlet with said source of the gas;
   with said tube for channeling the liquid received from said pressurizing device over said gas inlets to entrain the gas emanating therefrom as the bubbles, thereby forming the medium for communication from said outlet.

37. The method of claim 36 wherein said controller operates at least one of said pressurizing device and said source of the gas to produce an oscillatory component to the flow of at least one of the liquid and the gas.

38. The method of claim 1 wherein said bubble generator comprises:
   (a) a chamber defining a plurality of gas inlets in communication with said source of the gas via said at least one inlet; and
   (b) a liquid flow path defined within said chamber;
   with said liquid flow path for channeling the liquid received from said pressurizing device via said at least one inlet to an intersection with said gas inlets to entrain the gas emanating therefrom as the bubbles, thereby forming the medium for communication from said outlet.

39. The method of claim 38 wherein said controller operates at least one of said pressurizing device and said source of the gas to produce an oscillatory component to the flow of at least one of the liquid and the gas.

40. The method of claim 1 wherein said bubble generator comprises:
   (a) a first member having outer and inner sides, hydrophobic and hydrophilic, respectively, with a plurality of inlet holes extending therebetween, said outer side of said first member for channeling the liquid over said inlet holes;
   (b) a second member having inner and outer sides, hydrophobic and hydrophilic, respectively, with a plurality of outlet holes extending therebetween, said outer side of said second member for channeling the liquid over said outlet holes, said inner sides of said first and said second members being separated by a gap and arranged so that each of said inlet holes aligns with one of said outlet holes, said gap for channeling the gas between said first and said second members; and
   (c) a means for generating droplets of the liquid such that each of said droplets is directed through one of said inlet holes, said outlet hole corresponding thereto and the gas present therebetween and into the liquid on said outer side of said second member thereby forming a bubble therefrom within the liquid to form the medium therefrom.

41. The method of claim 1 wherein said bubble generator comprises:
   (a) a plate having a first surface and a second surface with an inlet hole extending therebetween, said first surface and a wall of said inlet hole being in contact with the liquid; and
   (b) a heater in communication with said wall of said inlet hole to form an interface assembly therefrom; such that, upon application of a pulse of energy to said heater, said heater heats the liquid in said inlet hole to form a bubble of gas therefrom, the bubble moving from said interface assembly into the liquid flowing along said second surface to form the medium therefrom.

42. A method of preparing a medium with bubbles formed therein and contemporaneous injection into a patient in connection with a medical procedure, the method including the steps of:
   (a) providing a source of a liquid and a source of a gas;
   (b) providing a bubble generator in which to form the medium by creating bubbles of the gas within the liquid, said bubble generator having at least one inlet for receiving the liquid and the gas from said sources thereof and an outlet from which the medium is output;
   (c) providing a pressurizing device for pressuring the liquid for conveyance into said bubble generator and thereby for conveying therefrom the medium formed therein; and
   (d) providing a controller for controlling at least said pressuring device and said bubble generator through which to control (I) a rate of flow of the liquid and a rate of flow of the gas into said bubble generator via said at least one inlet thereof, (II) at least one of a size, a concentration and a composition of the bubbles created by the bubble generator within the liquid and (III) a rate flow of the medium from the bubble generator via the outlet thereof; and (e) communicating from said bubble generator via said outlet thereof the medium immediately after formation thereof so as to inject the medium into the patient in connection with the medical procedure at a rate controlled by said controller.

43. A method of preparing a medium with bubbles formed therein and contemporaneous injection into a patient in connection with a medical procedure, the method including the steps of:

(a) providing a source of a first liquid;
(b) providing another source of at least one of a second liquid and a gas;
(b) providing a bubble generator wherein the bubbles are created using the gas and at least one of the first liquid and the second liquid to form the medium, said bubble generator having at least one inlet for receiving the first liquid and at least one of the second liquid and the gas from said sources thereof and an outlet from which the medium is output;
(c) providing a pressurizing device for pressuring the first liquid and at least one of the second liquid and the gas for conveyance into said bubble generator and thereby for conveying therefrom the medium formed therein; and
(d) providing a controller for controlling at least said pressuring device and said bubble generator through which to control (I) a rate of flow of the first liquid, a rate of flow of the second liquid and a rate of flow of the gas into said bubble generator via said at least one inlet thereof, (II) at least one property of the medium and (III) a rate flow of the medium from said bubble generator via said outlet thereof; and
(e) communicating from said bubble generator via said outlet thereof the medium immediately after formation thereof so as to inject the medium into the patient in connection with the medical procedure at a rate controlled by said controller.

44. The method of claim 43 wherein said bubble generator comprises:

(a) a liquid flow path for receiving and channeling the first liquid; and
(b) a gas flow path for directing the gas to said liquid flow path;
with said liquid and said gas flow paths constituting a gas-liquid interface assembly such that said liquid flow path channels the first liquid to an intersection with said gas flow path to entrain the gas emanating therefrom as the bubbles, thereby forming the medium communicated from said outlet.

45. The method of claim 44 wherein said controller operates said pressurizing device and said source of the gas to produce an oscillatory component to the flow within at least one of the gas flowing in said gas flow path and the first liquid flowing in said liquid flow path to promote uniformity in a size of the bubbles.

46. The method of claim 44 wherein said bubble generator comprises an array of said gas-liquid interface assemblies.

47. The method of claim 44 wherein said bubble generator further comprises a fluid flow path for receiving and channeling the second liquid into the first liquid into which the gas has been entrained, thereby further forming the medium communicated from said outlet.

48. The method of claim 47 wherein said bubble generator comprises an array of said gas-liquid interfaces.

49. The method of claim 43 wherein said bubble generator comprises:

(a) a first member having outer and inner sides, hydrophobic and hydrophilic, respectively, with a plurality of inlet holes extending therebetween, said outer side of said first member for channeling the first liquid over said inlet holes;
(b) a second member having inner and outer sides, hydrophobic and hydrophilic, respectively, with a plurality of outlet holes extending therebetween, said outer side of said second member for channeling the second liquid over said outlet holes, said inner sides of said first and said second members being separated by a gap and arranged so that each of said inlet holes aligns with one of said outlet holes, said gap for channeling the gas between said first and said second members; and
(c) a means for generating droplets of the first liquid such that each of said droplets is directed through one of said inlet holes, said outlet hole corresponding thereto and the gas present therebetween and into the second liquid thereby forming a bubble therefrom within the second liquid to form the medium therefrom.

50. The method of claim 43 wherein said bubble generator comprises:

(a) a housing having at least one cell chamber therein; and
(b) said at least one cell chamber defining therein a first liquid flow path, a second liquid flow path and a gas flow path, said first liquid flow path for receiving the first liquid, said second liquid flow path for receiving the second liquid, said gas flow path for receiving the gas;
wherein said gas flow path channels the gas received into an intersection of said flow paths at which the first and the second liquids meet so that, as a pulse of the second liquid arrives at said intersection, a bubble is (A) formed threat from the second liquid and the gas with the second liquid forming a shell of the bubble and (B) conveyed through said first liquid flow path into a flow of the first liquid outside of said cell chamber thereby forming the medium communicated from said outlet of said bubble generator.

51. The method of claim 43 wherein said bubble generator comprises:

(a) a plate having a first surface in contact with the first liquid and a second surface in contact with the second liquid with an inlet hole extending therebetween; and
(b) a heater in communication with a wall of said inlet hole to form an interface assembly therefrom; such that, upon application of a pulse of energy to said heater, said heater heats the first liquid in said inlet hole to form a bubble of gas therefrom, the bubble moving from said interface assembly into the second liquid to form the medium therefrom.

52. The method of claim 51 wherein the bubble incorporates components from the first liquid as it moves into the second liquid.

53. The method of claim 52 wherein:

(a) the first liquid is a hydrophobic liquid and the second liquid is hydrophilic liquid;
(b) said first surface and said wall of said plate is hydrophobic and in contact with the hydrophobic liquid, with the hydrophobic liquid comprising a first fluid and a second fluid with the first fluid having a boiling point lower than the second fluid; and
(c) said second surface is hydrophilic and in contact with the hydrophilic liquid;
such that, upon application of the pulse of energy to said heater, said heater heats the hydrophobic liquid in said inlet hole to form the bubble of gas from the first fluid thereof with the second fluid thereof condensing and forming a shell of the bubble with the bubble moving from said interface assembly into the hydrophilic liquid to form the medium therefrom.

\* \* \* \* \*

UNITED STATES PATENT AND TRADEMARK OFFICE
CERTIFICATE OF CORRECTION

PATENT NO. : 8,470,298 B2
APPLICATION NO. : 10/798876
DATED : June 25, 2013
INVENTOR(S) : Uber, III et al.

Page 1 of 1

It is certified that error appears in the above-identified patent and that said Letters Patent is hereby corrected as shown below:

IN THE SPECIFICATION:

1. In Column 19, Line 2, delete "3.3 n/sec" and insert -- 3.3 m/sec --, therefor.

IN THE CLAIMS:

2. In Column 30, Line 5, in Claim 16, delete "stifling" and insert -- stirring --, therefor.

Signed and Sealed this
Third Day of September, 2013

Teresa Stanek Rea
*Acting Director of the United States Patent and Trademark Office*